United States Patent [19]

Haviv et al.

[11] Patent Number: 5,491,217
[45] Date of Patent: Feb. 13, 1996

[54] LHRH ANTAGONISTS HAVING MODIFIED AMINOACYL RESIDUES AT POSITIONS 5 AND 6

[75] Inventors: Fortuna Haviv, Deerfield; Jonathan Greer, Chicago; Rolf E. Swenson, Grayslake; Daryl R. Sauer, Gurnee, all of Ill.

[73] Assignee: TAP Holding Inc., Abbott Park, Ill.

[21] Appl. No.: 282,411

[22] Filed: Jul. 28, 1994

Related U.S. Application Data

[63] Continuation of Ser. No. 993,202, Dec. 18, 1992, abandoned.

[51] Int. Cl.$^6$ ............... A61K 38/24; C07K 7/23
[52] U.S. Cl. ............................. 530/313; 530/328
[58] Field of Search ................... 530/328, 313; 514/15

[56] References Cited

U.S. PATENT DOCUMENTS

| | | |
|---|---|---|
| 4,317,815 | 3/1982 | Coy et al. . |
| 4,481,190 | 11/1984 | Nestor et al. . |
| 4,530,920 | 7/1985 | Nestor et al. . |
| 4,667,014 | 5/1987 | Nestor et al. . |
| 4,866,160 | 9/1989 | Coy et al. ............... 530/313 |
| 5,073,624 | 12/1991 | Coy et al. . |

FOREIGN PATENT DOCUMENTS

| | | |
|---|---|---|
| 0041286 | 12/1981 | European Pat. Off. . |
| WO91/06543 | 5/1991 | WIPO . |
| WO92/08733 | 5/1992 | WIPO . |
| WO92/13883 | 8/1992 | WIPO . |
| WO94/19370 | 9/1994 | WIPO ............... C07K 7/06 |

OTHER PUBLICATIONS

Abstract No. 869 from the 74th Annual Meeting Program and Abstracts of the Endocrine Society Meeting, San Antonio, TX, Jun. 24–27, 1992, C. A. Pampen, et al., "Characterization of a New Selective GnRH Antagonist with Potent Antiovulatory Activity and Extremely Low Anaphylactoid Activity".

Jean Rivier, et al., J. Med. Chem., 3 5: 4270–4278 (1992, "Gonadotropin–Releasing Hormone Antagonists with Nω–Triazolylornithine, –lysine, or –p–aminophenylalanine Residues at Positions 5 and 6."P. Theobald, et al., J. Am. Chem. Soc. 112: 9624–9626 (1990).

P. Theobald, et al., J. Am. Chem. Soc. 34: 2395–2402 (1991).

*Primary Examiner*—Jill Warden
*Assistant Examiner*—Benet Prickril
*Attorney, Agent, or Firm*—Jerry F. Janssen

[57] ABSTRACT

A class of potent LHRH decapeptide antagonists possess N-alkylated aminoacyl residues where the side-chain portion of the residue is a 4-(substimtedamino)phenylalanyl, 4-(substituted-amino)cyclohexylalanyl, or Ω-(substitutedamino)alkyl group, and additionally the aminoacyl residues at position 5 are N-alkylated on the nitrogen atom of the peptide backbone.

3 Claims, No Drawings

LHRH ANTAGONISTS HAVING MODIFIED AMINOACYL RESIDUES AT POSITIONS 5 AND 6

This application is a continuation of application Ser. No. 07/993,202, filed Dec. 18, 1992, now abandoned.

TECHNICAL FIELD

The present invention relates to organic compounds having biological activity, to pharmaceutical compositions containing these compounds, and to a medical method of treatment. More particularly, the present invention concerns certain peptides having LHRH antagonist activity, to compositions containing these peptides, and to a method of inhibiting LHRH activity in a mammal in need of such treatment.

BACKGROUND OF THE INVENTION

The gonadotropins, follicle stimulating hormone (FSH), luteinizing hormone (LH), and chorionic gonadotropin (CG) are required for ovulation, spermatogenesis, and the biosynthesis of sex steroids. A single hypothalamic hormone, gonadotropin-releasing hormone (GnRH, also known as luteinizing hormone-releasing hormone, LHRH) is responsible for regulating the secretion of both FSH and LH in mammals. LHRH has the structure

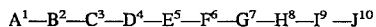

5-OxoPro—His—Trp—Ser—Tyr—Gly—Leu—Arg—Pro—GlyNH$_2$

In recent years considerable research effort has been expended on finding synthetic analogs of LHRH having equal or greater potency. These efforts have produced a number of LHRH agonists and antagonists. Attention has been particularly focused on modification of various positions to effect greater potency and in positions 5 and 6 to reduce the tendency of these LHRH analogs to stimulate histamine release.

SUMMARY OF THE INVENTION

It has been found, in accordance with the present invention that a class of potent LHRH decapeptide antagonists possess aminoacyl residues at positions 5 and 6 where the side-chain portion of the residue is a 4-(substituted-amino)phenylalanyl, 4-(substituted-amino)cyclohexylalanyl, or Ω-(substitutedamino)alkyl group. Additionally, the 5-position aminoacyl residues of the peptides of this invention are N-alkylated on the nitrogen atom of the peptide backbone.

In particular, the present invention provides a class of LHRH antagonist peptides which are characterized by the presence of N-alkyl aminoacyl residues and with modified N-alkyl-4-(substituted-amino)phenylalanyl or N-alkyl-4-(substituted-amino)cyclohexylalanyl residues at either position 5 or 6 in decapeptide LHRH analogs. In particular, the novel peptides of the present invention have the structure:

A$^1$—B$^2$—C$^3$—D$^4$—E$^5$—F$^6$—G$^7$—H$^8$—I$^9$—J$^{10}$ where each of the letters designates an aminoacyl residue.

A is an aminoacyl residue selected from the group consisting of N-acetyl-D-3-(2-naphthyl)alanyl; N-acetylsarcosyl; N-acetyl-D-phenylalanyl; N-acetyl-D(4-chlorophenyl)alanyl; N-acetyl-D-3-(3-quinolinyl)alanyl; and N-acetylazaglycyl.

B is an aminoacyl residue selected from the group consisting of D-phenylalanyl; D-3-(4-chlorophenyl)alanyl; D-3-(4-fluorophenyl)alanyl; and D-3-(2-naphthyl)alanyl.

C is an aminoacyl residue selected from the group consisting of D-3-(3-pyridyl)alanyl; D-3-(1-naphthyl)alanyl; D-3-(2-thiazolyl)alanyl; and D-3-(2-benzo[b]thienyl)alanyl.

D is an aminoacyl residue selected from the group consisting of L-seryl; and N-(R$^1$)-L-seryl where R$^1$ is straight or branched alkyl of from one to four carbon atoms.

E is an L-aminoacyl residue selected from the group consisting of

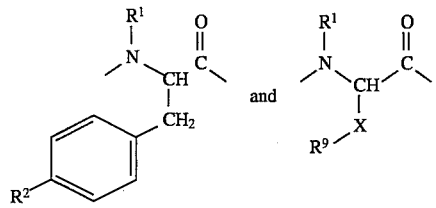

where R$^1$ is as defined above, and R$^2$ and R$^9$ have the values ascribed to them below.

R$^2$ is selected from (1) —NO$_2$; (2) —CH$_2$Cl; (3) —CH$_2$OH; (4) —CH$_2$OCH$_3$; (5) —CH$_2$N$_3$; (6) —CH$_2$CN; (7) —(CH$_2$)$_m$NR$^3$R$^4$ (where m is 1, or 2, R$^3$ and R$^4$ are independently selected from hydrogen, alkyl of from one to four carbon atoms, phenyl, and benzyl, or R$^3$ and R$^4$, taken together with the nitrogen atom to which they are attached, form a pyrrolidinyl, piperidinyl, morpholinyl, or N'-acetylpiperazinyl ring; with the proviso that when one of R$^3$ and R$^4$ is phenyl or benzyl, the other is hydrogen);

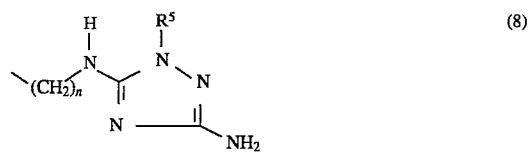

where n is 0, 1, or 2, and R$^5$ is hydrogen or alkyl of from one to four carbon atoms;

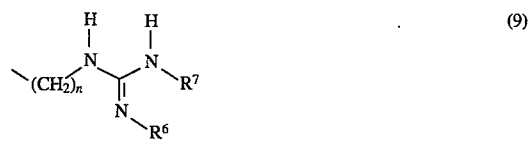

where n is 0, 1, or 2, R$^6$ and R$^7$ are independently hydrogen or alkyl of from one to four carbon atoms, or R$^6$ and R$^7$ together are —CH$_2$CH$_2$— or —CH$_2$CH$_2$CH$_2$—;

where m is as defined above and R$^8$ is selected from 2-, 3-, and 4-pyridinyl, 2- and 3-furyl, 2- and 3-thienyl, and 2-, 3-, and 4-quinolinyl.

X is 1,4-cyclohexylene or alkylene of from one to four carbon atoms, and R$^9$ is selected from (1) —(CH$_2$)$_m$NR$^3$R$^4$ where m, R$^3$ and R$^4$ are as defined above;

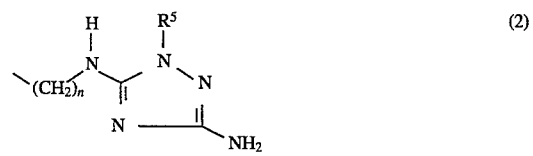

where n, and $R^5$ are as defined above;

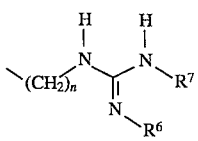 (3)

where n, $R^6$ and $R^7$ are as defined above; and

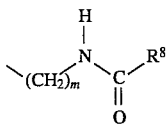 (4)

where m and $R^8$ are as defined above.

F is an aminoacyl residue selected from the group consisting of (a) D-tryptophanyl; (b) D-3-(3-pyridyl)alanyl; (c) D-seryl; (d) D-[epsilon-N-(N'-morpholinylcarbonyl)] lysyl; (e) D-[epsilon-N-(2-pyrazolinylcarbonyl)]lysyl; (f) D[ epsilon-N-(N'-piperidinylcarbonyl)]lysyl; (g) D-[epsilon-N-(3-quinolinylcarbonyl)] lysyl; (h) D-(epsilon-N-nicotinyl)ysyl; (i) D-citrullyl; (j) D-homocitrullyl; and (k) aminoacyl residues of the structures

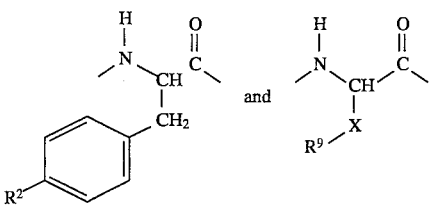

where $R^2$ and $R^9$ are as defined above.

G is an aminoacyl residue selected from the group consisting of (a) L-leucyl; (b) N-(R1)-L-leucyl; (c) L-valyl; (d) L-cyclohexylalanyl; (e) N-($R^1$)-L-cyclohexylalanyl; (f) L-iso-leucyl; and (g) ert-butylglycyl.

H is an aminoacyl residue selected from the group consisting of (a) L-(N-epsilon-isopropyl)lysyl; (b) L-arginyl; (c) L-homoarginyl; and (d) L-homoarginyl($N^G$,$N^{G'}$-diethyl).

I is an aminoacyl residue selected from the group consisting of (a) L-prolyl; and (b) N-$R^1$)-L-alanyl.

J is —$NHC_2H_5$ or an aminoacyl residue selected from the group consisting of (A) D-alaninamide; (B) N-$R^1$)-D-alaninamide; (C) N-$R^1$)-L-alaninamide; (D) sarcosamide; (e) α-aza-glycin-amide; and (e) D-serinamide; where $R^1$ is as defined above; with the proviso that when J is —$NHC_2H_5$, then I is L-prolyl.

Also contemplated as falling within the scope of the invention are the pharmaceutically acceptable addition salts of the above-defined peptides.

DETAILED DESCRIPTION

Definition

As used throughout this specification and the mended claims, the term "halide" as used herein refers to bromo (Br), chloro (Cl), fluoro (F) or iodo (D.

The terms "resin" or "peptide resin" as used herein refer to resins of the type commonly used in the art of synthetic peptide preparation. Examples of such resins include, but are not limited to, methyl benzhydrylamine (MBHA) or benzhydrylamine (BHA).

The term "alkyl" as used herein refers to divalent straight or branched group derived from a saturated hydrocarbon by the removal of a single hydrogen atom. Examples of alkyl include, but are not limited to methyl, ethyl, propyl, isopropyl, butyl, sec-butyl, iso-butyl, tert-butyl, pentyl, hexyl, and the like.

The term "alkylene" refers to a straight or branched divalent group derived from a saturated hydrocarbon by the removal of two hydrogen atoms. Examples of alkylene include —$CH_2$—, —$CH_2CH_2$—, —$CH(CH_3)CH_2$— and the like.

The term "cycloalkyl" refers to a monovalent cyclic hydrocarbon group derived from a cyclic saturated hydrocarbon group by the removal of a single hydrogen atom. Examples of cycloalkyl groups include cyclopropyl, cyclobutyl, cyclohexyl, cycloheptyl, bicyclo[2.2.2]octane, and the like.

The term "cycloalkylene" refers to a divalent group derived from a saturated cyclic hydrocarbon by the removal to two hydrogens. Examples include cyclopentylene, cycohexylene, and the like.

For the most part, the names of naturally-occuring and non-naturally-occuring aminoacyl residues used herein follow the naming conventions suggested by the IUPAC Commission on the Nomenclature of Organic Chemistry and the IUPAC-IUB Commission on Biochemical Nomenclature as set out in "Nomenclature of cc-Amino Acids (Recommendations, 1974)," *Biochemistry,* 14(2): 1975), which is incorporated herein by reference. To the extent that the names and abbreviations employed in this specification and appended claims differ from those suggestions, they will be made clear to the reader by the following table.

| Amino Acyl Residue Abbreviations | |
|---|---|
| Abbreviation | Definition |
| *Alanyl & Derivatives* | |
| Ala | L-Alanyl |
| D-Ala | D-Alanyl |
| L-AlaNH2 | L-Alanylamine |
| D-AlaNH2 | D-Alanylamide |
| N-Ac-Ala | N-Acetyl-L-alanyl |
| N-Ac-D-Ala | N-Acetyl-D-alanyl |
| 2-Bal | L-3-(Benzo[b]thien-2-yl)alanyl |
| 3-Bal | L-3-(Benzo[b]thien-3-yl)alanyl |
| D-2-Bal | D-3-(Benzo[b]thien-2-yl)alanyl |
| D-3-Bal | D-3-(Benzo[b]thien-3-yl)alanyl |
| N-Ac-2-Bal | N-Acetyl-L-3-(Benzo[b]thien-2-yl)alanyl |
| N-Ac-3-Bal | N-Acetyl-L-3-(Benzo[b]thien-3-yl)alanyl |

-continued

| Amino Acyl Residue Abbreviations | |
|---|---|
| Abbreviation | Definition |
| N-Ac-D-2-Bal | N-Acetyl-D-3-(Benzo[b]thien-2-yl)alanyl |
| N-Ac-D-3-Bal | N-Acetyl-D-3-(Benzo[b]thien-3-yl)alanyl |
| Cha | L-Cyclohexylalanyl |
| N-Ac-Cha | N-Acetyl-L-Cyclohexylalanyl |
| D-Cha | D-Cyclohexylalanyl |
| N-Ac-D-Cha | N-Acetyl-D-cyclohexylalanyl |
| 1-Nal | L-3-(Naphth-1-yl)alanyl |
| 2-Nal | L-3-(Naphth-2-yl)alanyl |
| D-1-Nal | D-3-(Naphth-1-yl)alanyl |
| D-2-Nal | D-3-(Naphth-2-yl)alanyl |
| N-Ac-1-Nal | N-Acetyl-L-3-(Naphth-1-yl)alanyl |
| N-Ac-2-Nal | N-Acetyl-L-3-(Naphth-2-yl)alanyl |
| N-Ac-D-1-Nal | N-Acetyl-D-3-(Naphth-1-yl)alanyl |
| N-Ac-D-2-Nal | N-Acetyl-D-3-(Naphth-2-yl)alanyl |
| 2-Pal | L-3-Pyrid-2-yl)alanyl |
| 3-Pal | L-3-(Pyrid-3-yl)alanyl |
| 4-Pal | L-3-(Pyrid-4-yl)alanyl |
| D-2-Pal | D-3-(Pyrid-2-yl)alanyl |
| D-3-Pal | D-3-(Pyrid-3-yl)alanyl |
| D-4-Pal | D-3-(Pyrid-4-yl)alanyl |
| N-Ac-2-Pal | N-Acetyl-L-3-(Pyrid-2-yl)alanyl |
| N-Ac-3-Pal | N-Acetyl-L-3-(Pyrid-3-yl)alanyl |
| N-Ac-4-Pal | N-Acetyl-L-3-(Pyrid-4-yl)alanyl |
| N-Ac-D-2-Pal | N-Acetyl-D-3-(Pyrid-2-yl)alanyl |
| N-Ac-D-3-Pal | N-Acetyl-D-3-(Pyrid-3-yl)alanyl |
| N-Ac-D-4-Pal | N-Acetyl-D-3-(Pyrid-4-yl)alanyl |
| 2-Qual | L-3-(Quinolin-2-yl)alanyl |
| 3-Qual | L-3-(Quinolin-3-yl)alanyl |
| 4-Qual | L-3-(Quinolin-4-yl)alanyl |
| D-2-Qual | D-3-(Quinolin-2-yl)alanyl |
| D-3-Qual | D-3-(Quinolin-3-yl)alanyl |
| D-4-Qual | D-3-(Quinolin-4-yl)alanyl |
| N-Ac-2-Qual | N-Acetyl-L-3-(Quinolin-2-yl)alanyl |
| N-Ac-3-Qual | N-Acetyl-L-3-(Quinolin-3-yl)alanyl |
| N-Ac-4-Qual | N-Acetyl-L-3-(Quinolin-4-yl)alanyl |
| N-Ac-D-2-Qual | N-Acetyl-D-3-(Quinolin-2-yl)alanyl |
| N-Ac-D-3-Qual | N-Acetyl-D-3-(Quinolin-3-yl)alanyl |
| N-Ac-D-4-Qual | N-Acetyl-D-3-(Quinolin-4-yl)alanyl |
| D-Thia or D-Thial | D-3-Thien-2-yl)alanyl |
| D-Thiaz | D-3-(Thiazol-4-yl)alanyl |
| D-(4-Atza)Phe | D-4-[5'(3'-amino-1H-1',2',4',-5'-triazolyl)amino]-phenylalanine |
| NMe(4-Atza)Phe | N-alpha-methyl-4-[5'(3'-amino-1H-1',2',4',-5'-triazolyl)amino]phenylalanine |
| NMe(4-Morphme)Phe | N-apha-methyl-4-(morpholino-N'-methyl)amino-phenylalanine |
| D-(4-Morphme)Phe | D-4-(morpholino-N'-methyl)aminophenylalanine |
| D-(4-Atzame)Phe | D-4-[5'(3'-amino-1H-1',2',4',-5'-triazolyl)methyl]amino-phenylalanine |
| NMe(4-Atzame)Phe | N-alpha-methyl-4-[5'(3'-amino-1H-1',2',4',-5'-triazolyl)methyl]amino]phenylalanine |
| D-(4-Atzaeth)Phe | D-4-[5'(3'-amino-1H-1',2',4',-5'-triazolyl)ethyl]amino-phenylalanine |
| NMe(4-Atzaeth)Phe | N-alpha-methyl-4-[5'(3'-amino-1H-1',2',4',-5'-triazolyl)ethyl]amino]phenylalanine |
| D-(4-Imame)Phe | D-4-(imidazolin-2-yl)aminomethylphenylalanine |
| NMe(4-Imame)Phe | N-alpha-4-(imidazolin-2-yl)aminomethylphenylalanine |
| D-(4-Nicame)Phe | D-4-(nicotinyl)aminomethylphenylalanine |
| NMe(4-NicamePhe | N-alpha-4-(nicotinyl)aminomethylphenylalanine |
| D-(4-Nicaeth)Phe | D-4-(nicotinyl)aminoethylphenylalanine |
| NMe(4-Nicaeth)Phe | N-alpha-4-(nicotinyl)aminoethylphenylalanine |
| D-(4-Etcng)Phe | D-4-($N^G$cyano,$N^G$ethyl-guanidino)phenylalanine |
| NMe(4-Etcng)Phe | N-alpha-methyl-4-($N^G$cyano,$N^G$ethylguanidino)-phenylalanine |
| D-4-N-(Nic)Cha | D-[4-(aminonicotinyl)cyclohexyl]alanyl |
| D-4-N-(Guan)Cha | D-[4-(guanidino)cyclohexylalanyl |
| Arginyl & Derivatives | |
| Arg | L-Arginyl |
| D-Arg | D-Arginyl |
| Harg | L-Homoarginyl (I.e. L-2-Amino-6-guanidinohexanoyl) |
| D-Harg | D-Homoarginyl (I.e. D-2-Amino-6-guanidinohexanoyl) |
| Harg(Et) | L-2-Amino-6-$N^G$-ethylguanidino- |

-continued

Amino Acyl Residue Abbreviations

| Abbreviation | Definition |
|---|---|
| | hexanoyl) |
| Harg(Et2) or | L-2-Amino-6-$N^G,N^{G'}$-diethylguanidino- |
| Harg(Diethyl) | hexanoyl) |
| N-MeHarg | N-Methyl-L-homoarginyl |

Glycyl & Derivatives

| | |
|---|---|
| Gly | Glycyl |
| N-Ac-Gly | N-Acetylglycyl |
| Aza-Gly | Azaglycyl |
| N-Ac-azaGly | N-Acetylazaglycyl |
| | alpha-amino-butyric acid |
| t-Bugly | α-tert-Butyl-glycyl |

Leucyl, Isoleucyl & Derivatives

| | |
|---|---|
| Ileu | L-Isoleucyl |
| D-Ileu | D-Isoleucyl |
| Leu | L-Leucyl |
| D-Leu | D-Leucyl |

Lysyl & Derivatives

| | |
|---|---|
| Lys | L-Lysyl |
| D-Lys | D-Lysyl |
| Lys(Isp) or Lys(Nisp) | L-(N'-epsilon-isopropyl)lysyl |
| D-Lys(Isp) or D-Lys(Nisp) | D-(N'-epsilon-isopropyl)lysyl |
| D-Lys(MePip)CO | D-(N'-epsilon-(N"-methyl-N-piperidinyl)carbonyl)lysyl |
| D-Lys(Morph)CO | D-(N'-epsilon(N"-Morpholino)carbonyl)lysyl |
| Lys(Nic) | L-(N'-epsilon-Nicotinyl)lysyl |
| D-Lys(Nic) | D-(N'-epsilon-Nicotinyl)lysyl |
| Lys(Pic) | L-(N'-epsilon-Picolyl)lysyl |
| Lys(chex) | L-(N'-epsilon-Cyclohexyl)lysyl |
| NMeLys(Nic) | N-Methyl-(N'-epsilon-nicotinyl)lysyl |

Miscellaneous

| | |
|---|---|
| Sar | Sarcosyl (I.e. N-Methylglycyl) |
| NAcSar | N-Acetyl-sarcosyl |

Ornithyl & Derivatives

| | |
|---|---|
| Orn | Ornithyl |
| | (I.e. α,δ-Diaminovaleryl) |
| D-Orn | D-Ornithyl |
| Cit | Citrullyl |
| | (I.e. N'-delta-Aminocarbonyl-L-ornithyl) |
| D-Cit | D-Citrullyl |
| Hcit | Homocitrullyl |
| | (I.e. L-2-Amino-(6-aminocarbonylamino)-hexanoyl |
| D-HCit | D-Homocitrullyl |

Phenylalanyl & Derivatives

| | |
|---|---|
| Phe | L-Phenylalanyl |
| D-Phe | D-Phenylalanyl |
| 4-Cl-Phe | L-3-(4-Chlorophenyl)alanyl |
| D-4-Cl-Phe | D-3-(4-Chlorophenyl)alanyl |
| 4-F-Phe | L-3-(4-Fluorophenyl)alanyl |
| D-4-F-Phe | D-3-(4-Fluorophenyl)alanyl |
| 4-$NO_2$-Phe | L-3-(4-Nitrophenyl)alanyl |
| D-4-$NO^2$-Phe | D-3-(4-Nitrophenyl)alanyl |
| N-Ac-Phe | N-Acetyl-L-phenylalanyl |
| N-Ac-D-Phe | N-Acetyl-D-phenylalanine |
| N-Ac-4-Cl-Phe | N-Acetyl-L-3-(4-Chlorophenyl)alanyl |
| N-Ac-D-4-Cl-Phe | N-Acetyl-D-3-(4-Chlorophenyl)alanyl |
| N-Ac-4-F-Phe | N-Acetyl-L-3-(4-Fluorophenyl)alanyl |
| N-Ac-D-4-F-Phe | N-Acetyl-D-3-(4-Fluorophenyl)alanyl |
| NMe(Isp)Phe | N-Methyl-3-[(4-Isopropylamino)]phenyl]alanyl |
| NMePha(Atz) | N-Methyl-{4-[5'-(3'-amino-1H-1',2',4'-triazolyl)phenyl]}alanyl |

Prolyl & Derivatives

| | |
|---|---|
| Pro | L-Prolyl |
| D-Pro | D-Prolyl |

Seryl & Derivatives

| | |
|---|---|
| Ser | L-Seryl |
| D-Ser | D-Seryl |

| Amino Acyl Residue Abbreviations | |
|---|---|
| Abbreviation | Definition |
| NMeHser | N-Methyl-Homoseryl |
| *Tryptophyl & Derivatives* | |
| Trp | L-Tryptyl |
| D-Trp | D-Tryptyl |
| *Tyrosyl & Derivatives* | |
| Tyr | L-Tyrosyl |
| N-Ac-Tyr | N-Acetyl-L-tyrosyl |
| D-Tyr | D-Tyrosyl |
| Tyr(OBz) | O-Benzyl-L-tyrosyl |
| Tyr(OMe) | O-Methyl-L-tyrosyl |
| D-Tyr(OBz) | O-Benzyl-D-tyrosyl |
| D-Tyr(OMe) | O-Methyl-D-tyrosyl |

Compounds contemplated as falling within the scope of the present invention include, but are not limited to, the following representative examples:

NAc—D-2Nal—D-4ClPhe—D-3Pal—Ser—NMe(4-NO₂)Phe—D—Cit—Leu—Arg—Pro—DAlaNH₂

NAc—D-2Nal—D-4ClPhe—D-3 Pal—Ser—NMe(4—NO₂)Phe—D—Lys(Nic)—Leu— Lys(Isp)—Pro—D—AlaNH₂;

NAc—D2Nal—D4ClPhe-D3Pal—Ser—NMe(4-Atza)Phe—DLys(Nic)—Leu— Lys(Isp)—Pro—DAlaNH₂;

NAc—D-2Nal—D-4ClPhe—D-3Pal—Ser—NMeTyr—D—(4-Atza)Phe—Leu— Lys(Isp)—Pro—D—AlaNH₂;

NAc—D-2Nal—D-4ClPhe—D-3 Pal-Set—NMe—(4-Atza)Phe—D—(4-Atza)Phe— Leu—Lys(Isp)—Pro—D—AlaNH₂;

NAc—D-2Nal—D—ClPhe—D-3Pal—Ser—NMe—(4-Atza)Phe—D—Lys(Nic)—Leu— Arg—Pro—DAlaNH₂;

NAc—D-2Nal—D-4ClPhe—D-3 Pal—Ser—NMe Tyr—D—(4-Atza)Phe—Leu—Arg— Pro—D—AlaNH₂;

NAc—D2Nal—D4ClPhe-D3Pal—Ser—NMe—(4-Atza)Phe—D—(4-Atza)Phe—Leu— Arg—Pro—DAlaNH₂;

NAc—Sar—D4ClPhe-D1Nal—Ser—NMe—(4-Atza)Phe—D—(4-Atza)Phe—Leu— Lys(Isp)—Pro—DAlaNH₂;

NAc—AzaGly—D4ClPhe-D1Nal—Ser—NMeTyr—D—(4-Atza)—Leu—Lys(Nisp)— Pro-DAIaNH₂;

NAc—D2Nal—D4ClPHe—D3Pal—Ser—NMe(4-Morphme)Phe—DLys(Nic)—Leu— Lys(Isp)—Pro—D AlaNH₂;

NAc—D2Nal—D4ClPhe—D3Pal—Ser—NMe(4-Morphme)Phe—D—(4-Morphme) Phe—Leu—Lys(Isp)—Pro—DAlaNH₂;

NAc—D2Nal—D4ClPhe—D3Pal—Ser—NMe-Tyr—D—(4-Morphine)Phe—Leu— Lys(Isp)—Pro—DAlaNH₂:

NAc—D2Nal—D4ClPhe—D3Pal—Ser—NMe(4-Morphme)Phe—DLys(Nic)—Leu— Arg—Pro—DAlaNH₂;

NAc—D2Nal—D4ClPhe—D3Pal—Ser—NMe-4(piperidino-N'-methyl)Phe— DLys(Nic)—Leu—Arg—Pro—D AlaNH₂;

NAc—D2Nal—D4ClPhe—D3Pal—Ser—NMe-4(pyrrolidino-N'-methyl)Phe— DLys(Nic)—Leu—Arg—Pro—DAlaNH₂;

NAc—D2Nal—D4ClPhe—D3Pal—Ser—NMe-4-(N'-acetyl-N"-piperazino-N'-methyl)Phe— DLys(Nic)— Leu—Arg—Pro—DAlaNH₂;

NAc—D2Nal—D4ClPhe—D3Pal—Ser—NMe-4-(diethyl-N'-methyl)Phe— DLys(Nic)—Leu—Arg—Pro—DAlaNH₂;

NAc—D2Nal—D4ClPhe—D3 Pal—Ser—NMe-4-(di-t-butyl-N'-methy)Phe— Lys(Nic )—Leu—Arg'Pro—D AlaNH₂;

NAc—D2Nal—D4ClPhe—D3Pal—Ser—NMe-4-(di-methyl-N'-methyl)Phe— DLys(Nic)—Leu—Arg—Pro—DAlaNH₂;

NAc—D2Nal'D4ClPhe—D3 Pal—Ser—NMe-4-(di-isopropyl-N'-methyl)Phe— DLys(Nic)—Leu—Arg—Pro—DAlaNH₂;

NAc—D2Nal—D4ClPhe—D3Pal—Ser—NMe-4-(di-propyl-N'-methy)Phe—DLys(Nic)— Leu—Arg—Pro—D AlaNH₂;

NAc—D2Nal—D4ClPhe—D3Pal—Ser—NMe-4-(propyl-N'-methyl)Phe— DLys(Nic)—Leu—Arg—Pro—D AlaNH₂;

NAc—D2Nal—D4ClPhe—D3Pal—Ser—NMe-4-(ethyl-N'-methyl)Phe— DLys(Nic)—Leu—Arg—Pro—D AlaNH₂;

NAc—D2Nal—D4ClPhe—D3Pal—Ser—NMe-4-(phenyl-N'-methyl)Phe— DLys(Nic)—Leu—Arg—Pro—DAlaNH₂;

NAc—D2Nal—D4ClPhe—D 3Pal—Ser—NMe-4-(benzyl-N'-methyl)PheD— Lys(Nic )—Leu—Arg—Pro—D AlaNH₂;

NAc—D2Nal—D4ClPhe—D 3 Pal—Ser—NMe-4-(p-chlorobenzyl-N'-methyl)Phe— DLys(Nic )—Leu-Arg-Pro—D AlaNH₂;

NAc—D2Nal—D4ClPhe—D3Pal—Ser—NMe-4-(p-fluorobenzyl-N'-methyl)Phe— DLys(Nic)—Leu—Arg—Pro—DAlaNH₂;

NAc—D2Nal—D4ClPhe—D3Pal—Ser—NMe-4-(p-nitrobenzyl-N'-methyl)Phe— DLys(Nic)—Leu—Arg—Pro—D AlaNH₂;

NAc—Sar—D4ClPhe—D1Nal—Ser—NMe—(4-Atza)Phe—D—Lys(Nic)—Leu— Lys(Isp)—Pro—DAlaNH₂;

NAc—D2Nal—D4ClPhe—D3Pal—Ser—NMe(4-Atzame)Phe—DLys(Nic)—Leu— Lys(Isp)—Pro—D AlaNH₂;

NAc—D2Nal—D4ClPhe—D3Pal—Ser—NMe(4-Atzame)Phe—DLys(Nic)—Leu— Lys(Isp)—Pro—DAlaNH₂;

NAc—D2Nal—D4ClPhe—D3 Pal—Ser—NMe(4-Atza)Phe—DLys(Nic)—Leu— Harg(Et₂)—Pro—D AlaNH₂;

NAc—D2Nal—D4ClPhe—D3Pal—Ser—NMe(4-Atza)Phe—D—(4-Atza)Phe—Leu— Harg(Et₂)—Pro—D AlaNH₂;

NAc—Sar—D4ClPhe—D3Bal—Ser—NMe—(4-Atza)Phe—D—(4-Atza)Phe—Leu— Lys(Isp)—Pro—D AlaNH₂;

NAc—Sar—D4ClPhe—D3Bal—Ser—NMe(4-Atza)Phe—D—Lys(Nic)—Leu— Lys(Isp)—Pro—DAlaNH₂;

NAc—Sar—D4ClPhe—D3Bal—Ser—NMeTyr—D—(4-Atza)Phe—Leu—Lys(Isp)—Pro— DAlaNH₂;

NAc—Sar—D4ClPhe—D-1Nal—Ser—NMe—(4-Atzame)Phe—D—(4-Atzame)Phe— Leu—Lys(Isp)—Pro—D AlaNH₂;

NAc—Sar—D4ClPhe—D-1Nal—Ser—NMe(4-Atzame-)Phe—D—Lys(Nic)—Leu— Lys(Isp)—Pro—DAlaNH₂;
NAc—Sar—D4ClPhe—D-1Nal—Ser—NMeTyr—D—(4-Atzame)Phe—Leu—Lys(Isp)— Pro—DAlaNH₂;
NAc—Sar—D4ClPhe—D-3Bal—Ser—NMe—(4-Atzame-)Phe—D—(4-Atzame)Phe— Leu—Lys(Isp)—Pro—D AlaNH₂;
NAc—Sar—D4ClPhe—D-3Bal—Ser—NMe(4-Atzame-)Phe—D—Lys(Nic)—Leu— Lys(Isp)—Pro—D AlaNH₂;
NAcAzaGly—D4ClPhe—D-3Bal—Ser—NMe—(4-Atza-)Phe—D—(4-Atza)Phe—Leu— Lys(Isp)—Pro—D AlaNH₂;
NAcAzaGly—D4ClPhe—D3Bal—Ser—NMe(4-Atza-)Phe—D—Lys(Nic)—Leu— Lys(Isp)—Pro—D AlaNH₂;
NAcAzaGly—D4ClPhe—D3Bal—Ser—NMeTyr—D—(4-Atza)Phe—Leu—Lys(Isp)— Pro—DAlaNH₂;
NAcAzaGly—D4ClPhe—D-1Nal—Ser—NMe—(4-Atzame)Phe—D—(4-Atzame) Phe—Leu —Lys(Isp)—Pro—DAlaNH₂;
NAcAzaGly—D4ClPhe—D-1Nal—Ser—NMe(4-Atzame-)Phe—D—Lys(Nic)—Leu— Lys(Isp)—Pro—D AlaNH₂;
NAcAzaGly—D4ClPhe—D—1Nal—Ser—NMeTyr—D—(4-Atzame)Phe—Leu— Lys(Isp)—Pro—DAlaNH₂;
NAcAzaGly—D4ClPhe—D-3Bal—Ser—NMe—(4-Atzame)Phe—D—(4-Atzame)Phe— Leu—Lys(Isp)—Pro—D AlaNH₂;
NAcAzaGly—D4ClPhe—D-3Bal—Ser—NMe(4-Atzame-)Phe—D—Lys(Nic)—Leu— Lys(Isp)—Pro—D AlaNH₂;
NAc—Sar—D4ClPhe—D-3Bal—Ser—NMeTyr—D—(4-Atzame)Phe—Leu—Lys(Isp)— Pro—DAlaNH₂;
NAc—D-2-Nal—D-4—Cl—Phe—D-3-Pal—Ser—NMeTyr—D—(4-Imame)—Phe—Leu— Lys(Isp)—Pro—DAlaNH₂;
NAc—D-2-Nal—D-4—Cl—Phe—D-3-Pal—Ser—NMe—(4-Imame)Phe—D—Lys(Nic)— Leu—Lys(Isp)—Pro—DAlaNH₂;
NAc—D-2-Nal—D-4—Cl—Phe—D-3-Pal—Ser—NMe—(4-Imame)Phe—D—(4-Imame) Phe—Leu—Lys(Isp)—Pro—DAlaNH₂;
NAc—D-2-Nal—D-4—Cl—Phe—D-3-Pal—Ser—NMe—Tyr—D—(4-Nicme)Phe—Leu— Lys(Isp)—Pro—D AlaNH₂;
NAc—D-2-Nal—D-4—Cl—Phe—D-3-Pal—Ser—NMe-Tyr—D—(4-Niceth)Phe—Leu— Lys(Isp)—Pro—D AlaNH2;
NAc—D-2-Nal—D-4—Cl—Phe—D-3-Pal—Ser—NMe—(4-Nicme)Phe—D—(4-Nicme) Phe—Leu—Lys(Isp)—Pro—DAlaNH2;
NAc—D-2-Nal—D-4-Cl-Phe—D-3-Pal—Ser—NMe—(4-Niceth)Phe—D—(4-Niceth) Phe—Leu—Lys(Isp)— Pro—DAlaNH2;
NAc—D2Nal—D4ClPhe—D3Pal—Ser—NMe(4-Etcng-)Phe—DLys(Nic)—Leu— Lys(Isp)—Pro—D AlaNH2;
NAc—D-2 Nal—D-4ClPhe—D-3 Pal—Ser—NMe Tyr—D—(4-Etcng)Phe—Leu— Lys(Isp)—Pro—D—AlaNH2; and
NAc—D-2Nal—D-4ClPhe—D-3Pal—Ser—NMe—(4-Etcng)Phe—D—(4-Etcng)Phe— Leu—Lys(Isp)—Pro—D—AlaNH2.

Preferred compounds of the present invention are those in which R² is selected from the group consisting of (a) —NO₂, (b) —CH₂OH, (c) —CH₂OCH3, and groups of the structure

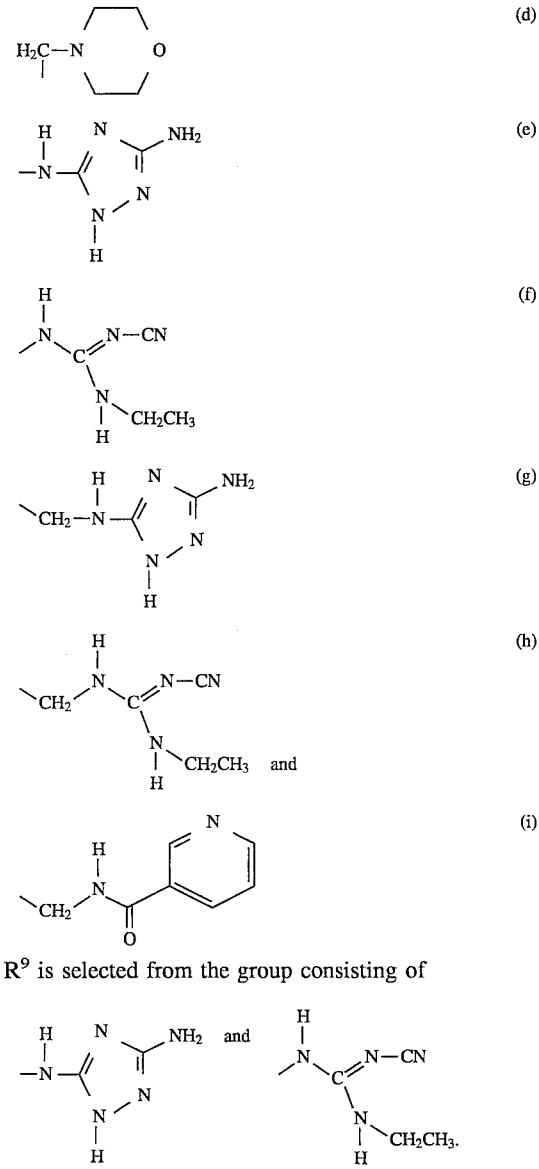

and R⁹ is selected from the group consisting of

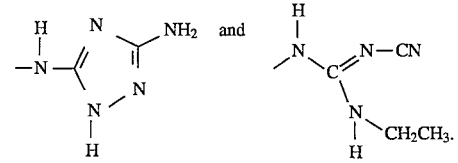

Particularly preferred compounds of the invention include
NAc—D-2Nal—D-4ClPhe—D-3 Pal—Set—NMe(4-NO₂)Phe—D—Cit—Leu—Arg—Pro— DAlaNH₂;
NAc—D-2Nal—D-4ClPhe—D-3 Pal—Set—NMe—(4-Atza)Phe—D—(4-Atza)Phe—Leu— Lys(Isp)—Pro—D—AlaNH₂;
NAc—D2Nal—D4ClPhe—D3Pal—Ser—NMe(4-Atza-)Phe—DLys(Nic)—Leu—Lys(Isp)— Pro—DAlaNH₂;
NAc—D-2Nal—D-4ClPhe—D-3Pal—Ser—NMeTyr—D—(4-Atza)Phe—Leu—Lys— Clsp)—Pro—D—AlaNH₂;
NAc—D-2Nal—D-4ClPhe—D-3Pal—Ser—NMe(4-NO₂)Phe—D—Lys(Nic)—Leu— Lys(Isp)—Pro—D—AlaNH₂;
NAc—Sar—D4ClPhe—D1Nal—Ser—NMe—(4-Atza-)Phe—D—(4-Atza)Phe—Leu— Lys(Isp)—Pro—D AlaNH₂;
NAc—D2Nal—D4ClPhe—D3 Pal—Set—NMe(4-Morphme)Phe—DLys(Nic)—Leu— Lys(Isp)—Pro—DAlaNH₂;
NAc—D2Nal—D4ClPhe—D3Pal—Ser—NMe(4-Atzame-)Phe—DLys(Nic)—Leu— Lys(Isp)—Pro—D AlaNH₂;

NAc—D2Nal—D4ClPhe—D3Pal—Ser—NMe(4-Atza-)Phe—DLys(Nic)—Leu— Harg(Et₂)—Pro—D AlaNH₂;

NAc—Sar—D4ClPhe—D1Nal—Ser—NMe—(4-Atza-)Phe—D—(4-Atza)Phe—Leu— Lys(Isp)—Pro—D AlaNH₂;

NAc—Sar—D4ClPhe—D1Nal—Ser—NMe(4-Atza)Phe—D—Lys(Nic)—Leu— Lys(Isp)—Pro—DAlaNH₂;

NAc—Sar—D4ClPhe—D1Nal—Ser—NMeTyr—D—(4-Atza)Phe—Leu—Lys(Isp)—Pro —DAlaNH₂;

NAc—Azagly-D4ClPhe—D1Nal—Ser—NMe—(4-Atza-)Phe—D—(4-Atza)Phe—Leu— Lys(Isp)—Pro— DAlaNH₂;

NAc—Azagly-D4ClPhe—D1Nal—Ser—NMe(4-Atza-)Phe—D—Lys(Nic)—Leu— Lys(Isp)—Pro—DAlaNH₂;

NAc—Azagly-D4ClPhe—D1Nal—Ser—NMeTyr—D—(4-Atza)Phe—Leu—Lys(Isp)— Pro—DAlaNH₂;

NAc—Sar—D4ClPhe—D3Bal—Ser—NMe—(4-Atza-)Phe—D—(4-Atza)Phe—Leu— Lys(Isp)—Pro—D AlaNH₂;

NAc—Sar—D4ClPhe—D3Bal—Ser—NMe (4-Atza)Phe— D—Lys(Nic)—Leu— Lys(Isp)—Pro—D AlaNH₂;

NAc—Sar—D4ClPhe—D3Bal—Ser—NMeTyr—D—(4-Atza)Phe—Leu—Lys(Isp)—Pro —DAlaNH₂;

NAc—D-2-Nal—D-4Cl-Phe—D-3-Pal—Ser—NMe-Tyr—D—(4-Nicme)Phe—Leu— Lys(Isp)—Pro— DAlaNH₂; and NAc—D-2 Nal—D-4ClPhe—D-3 Pal—Ser—NMe Tyr— D—(4-Etcng)Phe—Leu—Lys(Isp)— Pro—D—AlaNH₂.

LHRH Antagonist Activity

Representative compounds of the present invention were evaluated in in vitro tests for receptor binding ($pK_I$) and for LHRH antagonist potency ($pA_2$). The tests employed the methods detailed in F. Haviv, et al. *J. Med. Chem,*, 32: 2340–2344 (1989). The receptor binding affinities ($pK_I$) are the negative logarithms of the equilibrium dissociation constants, and the values of $pA_2$ are the negative logarithms of the concentration of antagonist which shift the response curve produced by the agonist leuprolide to two-fold higher concentration. (Leuprolide is the LHRH agonist having the structure 5-ox—Pro¹—His²—Trp³—Ser⁴— Tyr⁵—D—Leu⁶—Leu⁷—Arg⁸—Pro⁹—NHEt and is disclosed and claimed in U.S. Pat. No. 4,005,063.) Typically $pA_2$ values of 9.5 or greater are indicative of good LHRH antagonist potency.

The results of these tests for representative compounds in accordance with this invention are presented in Table 2.

TABLE 2

| Example | $pA_2$ |
|---|---|
| 1 | 11.26 |
| 3 | 11.22 |
| 4 | 10.35 |
| 5 | 10.68 |

The LHRH antagonists of the invention are also useful for controlling reproduction in both females and males. Compounds of the invention are useful for suppressing levels of gonadotropins and androgens.

In the practice of the method of this invention an effective amount of a compound of the invention or a pharmaceutical composition containing the antagonists is administered to the human or animal in need of, or desiring, such treatment. These compounds or compositions may be administered by any of a variety of routes depending upon the specific end use, including orally, parenterally (including subcutaneous, intramuscular and intraveneous administration), vaginally (particularly for contraception), rectally, buccally (including sublingually), transdermally or intanasally. The most suitable route in any given case will depend upon the use, particular active ingredient, the subject involved, and the judgment of the medical practitioner. The compound or composition may also be administered by means of slow-release, depot or implant formulations as described more fully herein below.

In general, to modulate levels of sex hormones in male or female mammals for the uses herein above described, it is expedient to administer the active ingredient in amounts between about 0.01 and 10 mg./kg body weight per day, preferably between about 0.1 and 5.0 mg/kg body weight per day. This administration may be accomplished by a single daily administration, by distribution over several applications or by slow release in order to achieve the most effective results.

The exact dose and regimen for administration of these compounds and compositions will necessarily be dependent upon the needs of the individual subject being treated, the type of treatment, the degree of affliction or need and the judgment of the medical practitioner. In general, parenteral administration requires lower dosage than other methods of administration which are more dependent upon absorption.

A further aspect of the present invention relates to pharmaceutical compositions containing as active ingredient a compound of the present invention which compositions comprise such compound in admixture with a pharmaceutically acceptable, non-toxic carder. As mentioned above, such compositions may be prepared for use for parenteral (subcutaneous, intramuscular or intraveneous) administration, particularly in the form of liquid solutions or suspensions; for use in vaginal or rectal administration, particularly in semisolid forms such as creams and suppositories; for oral or buccal administration, particularly in the form of tablets or capsules, or intranasally, particularly in the form of powders, nasal drops or aerosols.

The compositions may conveniently be administered in unit dosage form and may be prepared by any of the methods well-known in the pharmaceutical art, for example as described in Remington's Pharmaceutical Sciences, Mack Publishing Company, Easton, Pa., 1970. Formulations for parentera administration may contain as common excipients sterile water or saline, polyalkylene glycols such as polyethylene glycol, oils of vegetable origin, hydrogenated naphthalenes and the like. Formulations for inhalation administratiom may be solid and contain as excipients, for example, lactose, or may be aqueous or oily solutions for administration in the form of nasal drops. For buccal administration typical excipients include sugars, calcium stearate, magnesium stearate, pregelatinated starch, and the like.

It is particularly desirable to deliver the compounds of the present invention to the subject over prolonged periods of time, for example, for periods of one week to one year from a single administration. Various slow release, depot or implant dosage forms may be utilized. For example, a dosage form may contain a pharmaceutically acceptable non-toxic salt of a compound of the invention which has a low degree of solubility in body fluids, for example, (a) an acid addition salt with a polybasic acid such as phosphoric acid, sulfuric acid, citric acid, tartaric acid, tannic acid, pamoic acid, alginic acid, polyglutamic acid, naphthalene mono- or di-sulfonic acids, polygalacturonic acid, and the like; (b) a salt with a polyvalent metal cation such as zinc, calcium, bismuth, barium, magnesium, aluminum, copper, cobalt, nickel, cadmium and the like, or with an organic cation formed from e.g., N,N'-dibenzylethylenediamine or ethylenediamine; or (c) combinations of (a) and (b) e.g. a zinc tannate salt. Additionally, the compounds of the present invention or, preferably, a relatively insoluble salt such as those just described, may be formulated in a gel, for example, an aluminum monostearate gel with, e.g. sesame oil, suitable for injection. Particularly preferred salts are zinc salts, zinc tannate salts, pamoate salts, and the like. Another type of slow release depot formulation for injection would contain the compound or salt dispersed or encapsulated in a slow degrading, non-toxic, non-antigenic polymer such as a polylactic acid/polyglycolic acid polymer for example as described in U.S. Pat. No. 3,773,9 19. The compounds of the invention or, preferably, relatively insoluble salts such as those described above may also be formulated in cholesterol matrix pellets, particularly for use in animals. Additional slow release, depot or implant formulations, e.g. liposomes, are well known in the literature. See, for example, Sustained and Controlled Release Drug Delivery Systems, J. R. Robinson ed., Marcel Dekker, Inc., New York, 1978. Particular reference with respect to LHRH type compounds may be found, for example, in U.S. Pat. No. 4,010,125.

Synthesis of the Compounds of the Invention

In general, the compounds of the present invention are synthesized by techniques known to those skilled in the art as, for example, by so-called "solid phase" peptide synthesis or by usual methods of solution chemistry. A summary of available solid phase peptide synthetic techniques may be found in J. M. Stewart and J. D. Young, *Solid Phase Peptide Synthesis,* W.H. Freeman Co., San Francisco, 1963 and J. Meienhofer, *Hormonal Proteins and Peptides,* Vol. 2., p.46, Academic Press (New York), 1973. For classical solution synthesis see G. Schroder and K. Lupke, *The Peptides, vol.* 1, Academic Pres (New York), 1965.

In general, these methods comprise the sequential addition of one or more amino acids or suitably protected amino acids to a growing peptide chain bound to a suitable resin. The starting amino acids are commercially available or, where novel in the compounds of this invention, are synthesized by methods detailed below from readily available starting materials.

Normally, either the amino or carboxyl group of the first amino acid is protected by a suitable protecting group. The protected or derivatized amino acid can then be either attached to an inert solid support (resin) or utilized in solution by adding the next amino acid in the sequence having the complimentary (amino or carboxyl) group suitably protected, under conditions conducive for forming the amide linkage. The protecting group is then removed from this newly added amino acid residue and the next amino acid (suitably protected) is added, and so forth.

After all the desired amino acids have been linked in the proper sequence, any remaining protecting groups are removed sequentially or concurrently, and the peptide chain, if synthesized by the solid phase method, is cleaved from the solid support to afford the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide.

A particularly preferred method of preparing peptides involves solid phase peptide synthesis. In this method of preparing peptides, the alpha-amino function is of the amino acids is protected by an acid or base sensitive group. Such protecting groups should have the properties of being stable to the conditions of peptide linkage formation, while being readily removable without destruction of the growing peptide chain or racemization of any of the chiral centers contained therein. Suitable protecting groups are t-butyloxycarbonyl (BOC), benzyloxycarbonyl (Cbz), biphenylisopropyloxycarbonyl, t-amyloxycarbonyl, isobornyloxycarbonyl, (alpha,alpha)-dimethyl-3,5dimethoxybenzyloxycarbonyl, o-nitrophenylsulfenyl, 2-cyano-t-butyloxycarbonyl, 9-fluorenylmethyloxycarbonyl and the like. The t-butyloxycarbonyl ("BOC" or "t-BOC") protecting group is preferred.

Particularly preferred side chain protecting groups are, for side-chain amino groups as in lysine and arginine: nitro, p-toluene-sulfonyl, 4-methoxybenzene-sulfonyl, Cbz, BOC and adamantyloxycarbonyl; for tyrosine: benzyl, o-bromobenzyloxycarbonyl, 2,6-dichlorobenzyl, isopropyl, cyclohexyl, cyclopentyl and acetyl; for serine: benzyl and tetrahydropyranyl; for histidine: o benzyl, Cbz, p-toluenesulfonyl and 2,4-dinitrophenyl; for tryptophan: formyl.

In the solid phase peptide synthesis method, the C-terminal amino acid is attached to a suitable solid support. Suitable solid supports useful for the above synthesis are those materials which are inert to the reagents and reaction conditions of the stepwise condensation-deprotection reactions, as well as being insoluble in the solvent media used. Suitable solid supports are chloromethylpolystyrene-divinylbenzene polymer, hydroxymethyl-polystyrene-divinylbenzene polymer, and the like. Chloromethyl-polystyrene-1% divinylbenzene polymer is especially preferred. For the special case where the C-terminus of the compound is glycinamide, a particularly useful support is the benzhydrylamino-polystyrene-divinylbenzene polymer described by P. Rivaille, et al, *Helv. Chim. Acta.,* 54, 2772(1971). The coupling to the chloromethyl polystyrene-divinylbenzene type of resin is made by means of the reaction of the alpha-N-protected amino acid, especially the BOC-amino acid, as its cesium, tetramethylammonium, triethylammonium, 1,5-diazabicyclo-[5.4.0]undec-5-ene, or similar salt. The coupling reaction is accomplished in a solvent such as ethanol, acetonitrile, N,N-dimethylfonnamide (DMF), and the like, with the chloromethyl resin at an elevated temperature, for example between about 40° and 60° C., for from about 12 to 48 hours. Preferred reagents and reaction conditions involve the coupling of an alpha-N-BOC amino acid cesium salt with the resin in DMF at about 50° C for about 24 hours. The alpha-N-BOC-amino acid is attached to the benzhydrylamine resin by means of N,N'-dicyclohexylcarbodiimide (DCC) or N,N'-diisopropylcarbodiimide (DIC) with or without 1-hydroxybenzotriazole (HOBt), benzotriazol-1-yloxy-tris(dimethylamino)phosphonium-hexafluorophosphate (BOP) or bis(2-ox-3-oxazolidinyl)phosphine chloride (BOPCl), mediated coupling for from about 1 to about 24 hours, preferably about 12 hours at a temperature of between about 10° and 50° C., most preferably 25° C. in a solvent such as dichloromethane or DMF, preferably dichloromethane. The coupling of the carboxyl group to the N-methyl—Ser(OBzl) attached to the peptide resin requires catalysis by 4-dimethylaminopyridine (DMAP), in addition to the carbodiimide reagent.

The coupling of successive protected amino acids can be carried out in an automatic polypeptide synthesizer as is well known in the art. The removal of the alpha-N-protecting groups may be performed in the presence of, for example, a solution of trifluoroacetic acid in methylene chloride, hydrogen chloride in dioxane, hydrogen chloride in acetic acid, or other strong acid solution, preferably 50% trifluoroacetic acid in dichloromethane at about ambient temperature. Each protected amino acid is preferably introduced in 0.4M concentration and approximately 3.5 molar excess and the coupling may be carded out in dichloromethane, dichloromethane/DMF mixtures, DMF and the like, especially in methylene chloride at about ambient temperature. The coupling agent is normally DCC in dichloromethane but may be N,N'-di-isopropylcarbodiimide (DIC) or other carbodiimide either alone or in the presence of HOBt, N-hydroxysuccinimide, other N-hydroxyimides or oximes. Alternately, protected amino acid active ester (e.g. p-nitrophenyl, pentafluorophenyl and the like) or symmetrical anhydrides may be used.

The side-chain modifications at positions 5 and 6 of the peptides of the present invention are carried out by methods detailed below in Preparations A–G.

Preparation A

N-(t-Butoxycarbonyl)-N-Methyl-[4-(Morpholino-N'-methyl)]Phenylalanine

BOC—N—Me—(4-chloromethyl)phenylalanine is synthesized from BOC—N—MePhe using a synthetic procedure analogous to the one described in U.S. Pat. No. 4,026,887 for 4-(chloromethyl)phenylalanine.

A mixture of N-trifluoroacetyl-N-methyl-phenylalanine (1 equivalent) and zinc chloride (0.9 to 2.2 equivalents) in chloromethylether is heated at 65° C. for 10–24 hr. The excess reagent is removed in vacuo and the residue is dissolved in $CH_2Cl_2$, washed with saturated $NaHCO_3$ solution, then with saturated sodium chloride solution. The organic phase is dried ($Na_2SO_4$) and concentrated. The crude product is purified by column chromatography to yield the 4(chloromethyl)phenylalanine methyl ester. This is treated with aqueous hydrochloric acid to cleave the methyl ester. The N-methyl-(4chloromethyl)phenylalanine hydrochloride is treated with di-t-butylcarbonate (1.2 equivalents) in the presence of triethylamine (1 equivalent) in THF at 0° C. for 1 hr. After work-up and purification BOC-N-methyl-(4-chloromethyl)phenylalanine is obtained. This is dissolved in ethanol in the presence of excess morpholine and heated at 60–100° C. for 2 hr. Following work-up and purification BOC—N— methyl-(4-morpholinomethyl)phenylalanine is obtained. This is treated with one equivalent of p-toluenesulfonic acid to yield BOC—NMe-4(Morpholinomethyl)phenylalanine p-toluenesulfonate salt, which subsequently is used in the peptide solid phase synthesis.

Preparation B

When the procedure described in preparation A is used but the appropriate amines or secondary amines are substituted for morpholine, the following amino acids are obtained as the tosylate salts and subsequently used in the synthesis of LHRH antagonists of the present invention:

N-(t-Butoxycarbonyl)-N-methyl-[4-(piperidino)N'-methyl]-phenylalanine.
N-(t-Butoxycarbonyl)-N-methyl-[4-(N-pyrrolidino)N'-methyl]phenylalanine.
N-(t-Butoxycarbonyl)-N-methyl-[4-(N'-acetyl-piperazino-N"-methyl)) phenylalanine.
N-(t-Butoxycarbonyl)-N-methyl-[4-(di-ethylamino)-N'-methyl]phenylalanine.
N-(t-Butoxycarbonyl)-N-methyl-[4-(di-t-butylamino)-N'-methyl]phenylalanine.
N-(t-Butoxycarbonyl)-N-methyl-[4-(di-methylamino)-N'-methyl]phenylalanine.
N-(t-Butoxycarbonyl)-N-methyl-[4-(di-isopropylamino)N'-methyl]phenylalanine.
N-(t-Butoxycarbonyl)-N-methyl-[4-(N-propylamino) N'-methyl]phenylalanine.

Preparation C

N-(t-Butoxycarbonyl)—D—[4-(Morpholino)-N'-methyl]Phenylalanine

The procedure described in preparation B is used but substituting BOC—N—D—Phe for BOC—N—Me—Phe. After work-up and purification N-(t-butoxycarbonyl)-N—D—[4-(morpholino)-N'-methyl]phenylalanine is obtained as the tosylate salt.

Preparation D

When the procedure described in preparation C is use but morpholine is substituted with the appropriate primary and secondary amines the following D-amino acids are obtained as the tosylate salts and subsequently used in the synthesis of LHRH antagonists:

N-(t-Butoxycarbonyl)-D-(4-(piperidino-N'-methyl))phenylalanine.
N-(t-Butoxycarbonyl)-D-(4-(pyrrolidino-N'-methyl))phenylalanine.
N-(t-Butoxycarbonyl)-D-(4-(N'-acetyl)-N"-piperazinomethyl))phenylalanine.
N-(t-Butoxycarbonyl)-D-(4-(di-ethyl)-N'-methyl))phenylalanine.
N-(t-Butoxycarbonyl)-D-(4-(di-t-butyl)-N'-methyl))phenylalanine.
N-(t-Butoxycarbonyl)-D-(4-(di-methyl)-N'-methyl))phenylalanine.
N-(t-Butoxycarbonyl)-D-(4-(di-isopropyl)-N'-methyl))phenylalanine.
N-(t-Butoxycarbonyl)-D-(4-(propyl)methyl)-N'-phenylalanine.
N-(t-Butoxycarbonyl)-D-(4-(ethyl)methyl)-N'-phenylalanine.
N-(t-Butoxycarbonyl)-D-(4-(phenyl)methyl)-N'-phenylalanine.
N-(t-Butoxycarbonyl)-D-(4-(benzyl)methyl)-N'-phenylalanine.
N-(t-Butoxycarbonyl)-D-{4-[p-chloro-benzyl]-N'-methyl}phenylalanine.
N-(t-Butoxycarbonyl)-D-{4-[p-fluoro-benzyl]-N'-methyl}phenylalanine.
N-(t-Butoxycarbonyl)-D-{4-[p-nitro-benzyl]-N'-methyl}phenylalanine.

Preparation E

N-(t-Butoxycarbonyl)-N-Methyl-(4-FMOC-aminomethyl)Phenylalanine

BOC—N—Me—(4-chloromethyl)phenylalanine, obtained according to the procedure described in Preparation A, is heated under reflux for 4 to 24 hr with excess of sodium azide and catalytic amount of sodium iodide in methanol. The residue is treated with dilute hydrochloric acid to pH 6 and extracted with ethyl acetate. The organic extracts are dried and concentrated to yield BOC-N-methyl(4-azidomethyl)phenylalanine. This is hydrogenated over Pd/C catalyst in methanol to afford BOC-N-methyl-(4-aminomethyl)phenylalanine. The last compound is treated with 9-fluorenylmethyl chlorocarbonate under basic conditions as described in page 24 of "The Practice of Peptide Synthesis" by M. Bodanszky and A. Bodanszky. After work-up and purification N-(t-butoxycarbonyl)-N-methyl-(4-FMOC-aminomethyl)phenylalanine is obtained (see Scheme 1).

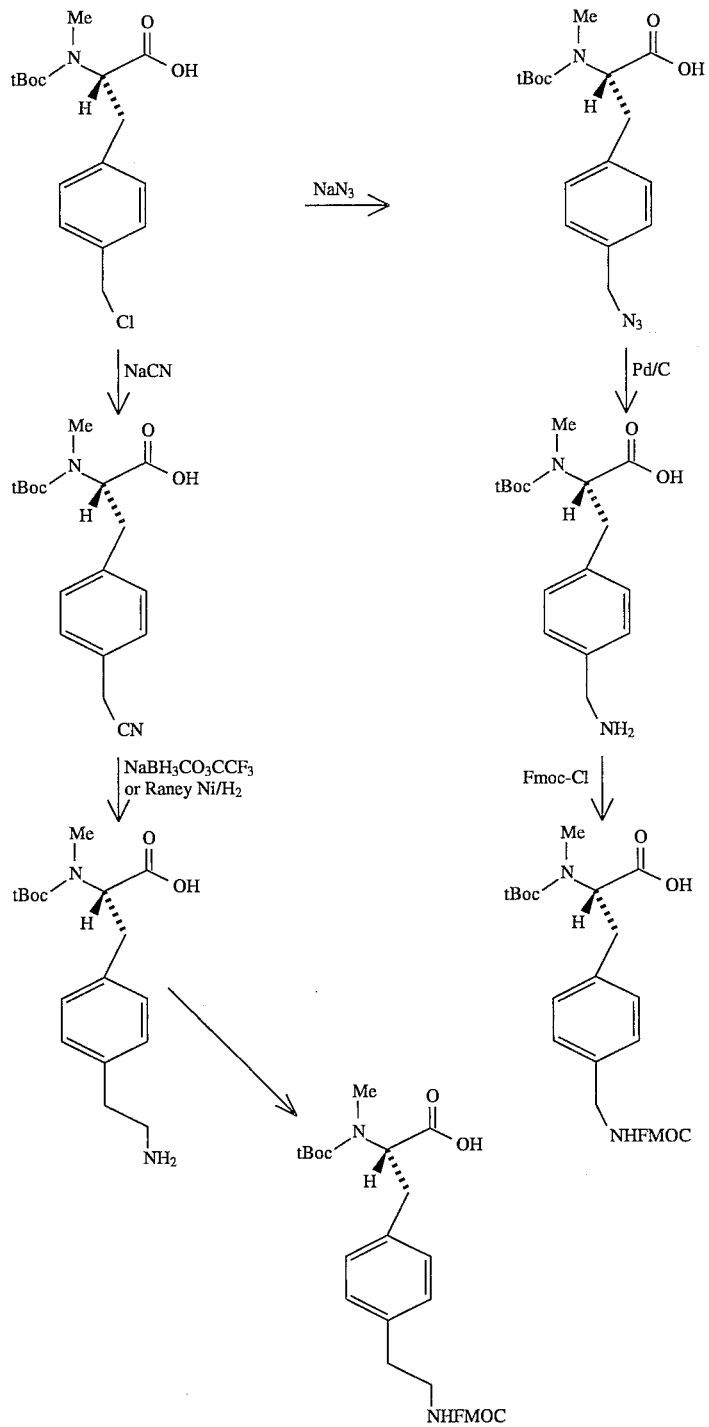

Scheme 1

Preparation F

N-(t-Butoxycarbonyl)-D-(4-FMOC-aminomethyl)Phenylalanine

BOC—D—(4-chloromethyl)phenylalanine is synthesized according to Preparation C described above. The product is first treated with sodium azide in methanol, using analogous conditions to those described in Preparation E, and then hydrogenated to yield N—BOC—D—(4-aminomethyl)phenylalanine which is substituted with FMOC, as previously described, to afford N-(t-Butoxycarbonyl)-D-( 4-FMOC-aminomethyl)Phenylalanine.

Preparation G

N-(t-Butoxycarbonyl)-N-Methyl-(4-FMOC-aminoethyl)Phenylalanine

BOC—N—Me—(4-chloromethyl)phenylalanine, obtained according to the procedure described in Preparation A, is heated under reflux for 4 to 24 hr with excess of sodium cyanide and catalytic amount of sodium iodide in methanol. The residue is treated with dilute hydrochloric acid to pH 6, and extracted with ethyl acetate. The organic extracts are dried and concentrated to yield BOC-N-methyl( 4-cyanomethyl)phenylalanine. This is hydrogenated over Raney/Ni catalyst in methanol or treated with sodium trifluoroacetoxyborohydride in THF [N. Umino et. al, Tetrahedron Letters 2875–2826(1976)]to afford BOC-N-methyl-(4-aminoethyl)phenylalanine. The last compound is treated with 9-fluorenylmethyl chlorocarbonate under basic conditions as described on page 24 of "The Practice of Peptide Synthesis" by M. Bodanszky and A. Bodanszky. After work-up and purification N-(t-butoxycarbonyl)-N-methyl-(4-FMOC-aminoethyl)phenylalanine is obtained. See Scheme 2.

EXAMPLE 1

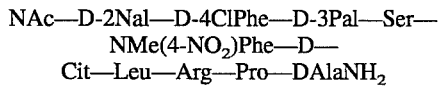
NAc—D-2Nal—D-4ClPhe—D-3Pal—Ser—NMe(4-NO₂)Phe—D—Cit—Leu—Arg—Pro—DAlaNH₂

In the reaction vessel of a Milligen-Biosearch 9500 peptide synthesizer was placed 1 g (0.6 mmol) of D—Ala—NH-resin (4-methyl-benzhydrylamine resin). Amino acids were added sequentially according to the following synthetic cycle:

1. Deblocking, to remove the t-BOC group from the alpha-amino function of the peptide, was carried out using a solution of 45% trifluoroacetic acid (TFA), 2.5% anisole, 2.0% dimethyl phosphite, and 50.5% methylene chloride. The resin was prewashed with the deblocking solution for one minute and then the deblocking reaction was run for 20 minutes.

2. Base wash, to remove and neutralize the TFA used for deprotection, was carded out using a solution of 10% N,N'-diisopropylethylamine in methylene chloride. The resin was washed with base three times for one minute each time after a deblocking step.

3. Coupling reaction was carried out using a 3-fold molar excess of 0.3 M DMF lo solution of a t-BOC protected amino acid derivative along with a 3-fold molar excess of 0.3M methylene chloride solution of diisopropylcarbodiimide as activator. The activated amino acid was then coupled to the free alpha amino group of the peptide-resin. The reaction time was as described in the synthesis protocol.

4. Wash, each reaction step was followed by three washes of one minute each: one of methylene chloride, one of (1:1) methylene chloride/DMF, and one of DMF.

Synthesis Protocol

The amino protected amino acids were coupled to the resin according to the following order, number, and duration of couplings:

| # | Amino Acid Coupling | |
|---|---|---|
| 1. | BOC-Pro | two-1h |
| 2. | BOC-Arg(Tos) | two-1h |
| 3. | BOC-Leu | two-1h |
| 4. | BOC-D-Cit | two-1h |
| 5. | BOC-NMe-(4-NO₂)Phe | two-1h |
| 6. | BOC-Ser(OBzl) | two-1h |
| 7. | BOC-D-3Pal | two-6h |
| 8. | BOC-D-4ClPhe | two-2h |
| 9. | BOC-D2Nal | two-2h |
| 10. | Acetic acid | two-2h |

Upon completion of the synthesis the peptide-resin was then dried overnight over P₂O₅ under vacuum and then treated with dry HF in the presence of anisole at 0° C. for 1.25 h to cleave the peptide from the resin. The excess of reagent was removed in vacuo. The resin was washed first with ether, then stirred at room temperature with a solution of (1:1:0.1) water/acetonitrile/acetic acid (50 ml) for 15 minutes, and filtered. The filtrate was lyophilized to give the crude peptide as a fluffy powder. This was purified by HPLC using a (25×2.5 cm) Dynamax C-18 column (8 micron) with solvent mixtures varying in a gradient ranging from 89% H₂O/11% CH₃CN/0.1% TFA over a period of 20 minutes. The UV detector was set at 260 nM. The product was eluted at 40.40 min as a single peak, collected and lyophilized to give pure NAc—D2Nal—D4ClPhe—D3Pal—Ser—NMe(4NO₂)Phe—DCit—Leu—Arg—Pro—DAlaNH₂ as the trifluoroacetate salt. FAB Mass spec. m/e 1473.(M+H)⁺. Amino Acid Anal: 1.01 Ala; 1.03 Pro; 0.95 Arg; 1.01 Leu; 1.00 Cit; 0.42 Ser; 1.05 3 Pal; 1.09 4ClPhe.

EXAMPLE 2

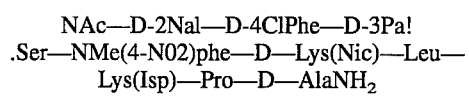
NAc—D-2Nal—D-4ClPhe—D-3Pa!.Ser—NMe(4-N02)phe—D—Lys(Nic)—Leu—Lys(Isp)—Pro—D—AlaNH₂

The procedure described in Example 1 is used but substituting BOCD—Lys(Nic) for BOC—D—Cit and BOC—Lys(Isp,Cbz) for BOC—ArgCFos). Upon the completion of the synthesis the peptide-resin is dried over P₂O₅ overnight and subsequently is treated with HF/anisole using the conditions described above. After work-up and lyophilization the peptide is purified by HPLC to yield NAc—D- 2Nal—D-4ClPhe—D-3Pal—Ser—NMe(4-NO₂)Phe—D—Lys-(Nic)—Leu—Lys(Isp)—Pro—D— AlaNH₂ as the trifluoroacetate salt.

EXAMPLE 3

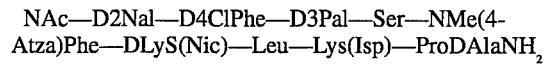
NAc—D2Nal—D4ClPhe—D3Pal—Ser—NMe(4-Atza)Phe—DLyS(Nic)—Leu—Lys(Isp)—ProDAlaNH₂

The procedure described in Example 2 is used but substituting BOC—NMe—(4-NO ₂)Phe with BOC—NMe—(4-FMOC-amino)Phe. Upon the completion of the synthesis the peptide-resin is heated with 30% piperidine/DMF for 2 to 24 hr, to cleave the FMOC group from the N-4-amino position of the N-Me-Phe⁵ residue. The peptide-resin is washed, 3 times with methylene chloride, 3 times with DMF, and reacted with 10- to 20-fold excess of diphenylcyanocarboimidate in DMF overnight (see Scheme 2 below), washed, 3 times with methylene chloride, 3 times with DMF, and then reacted with 20- to 100-fold excess of hydrazine in DMF overnight. The peptide-resin is washed, as previously described, dried over P$_2$O$_5$ overnight, and treated with HF/anisole as above. After work-up and lyophilization the crude product is obtained. This product is purified by HPLC to yield NAc— D2Nal—D4ClPhe—D3Pal—Ser—NMe(4-Atza)Phe—DLysCNic)—Leu—Lys(Isp)—ProDAlaNH$_2$ as the trifluoroacetate salt. R$_f$=20.56 rain; FAB Mass Spec. m/e 1615 (M+H). Amino acid anal.: 1.03 Ala; 0.98 Pro; 1.02 Lys(Isp); 0.98 Leu; 1.00 Lys; 0.51 Ser.

overnight. The peptide-resin is again washed, as previously described, dried over P$_2$O$_5$ overnight, and treated with HF/anisole as above. After work-up and lyophilization the crude product is obtained. This product is purified by HPLC to yield NAc—D-2Nal—D—ClPhe—D- 3Pal—Ser—NMeTyr—D—(4-Atza)Phe—Leu—Lys(Isp)—Pro—DAlaNH$_2$. R$_f$=17.61 min; FAB Mass Spec. m/e 1545 (M+H). Amino acid anal.: 1.01 Ala; 1.00 Pro; 0.91 Lys(Isp); 1.00 Leu; 1.05 NMeTyr; 0.50 Ser; 0.98 3Pal; 1.00 4ClPhe.

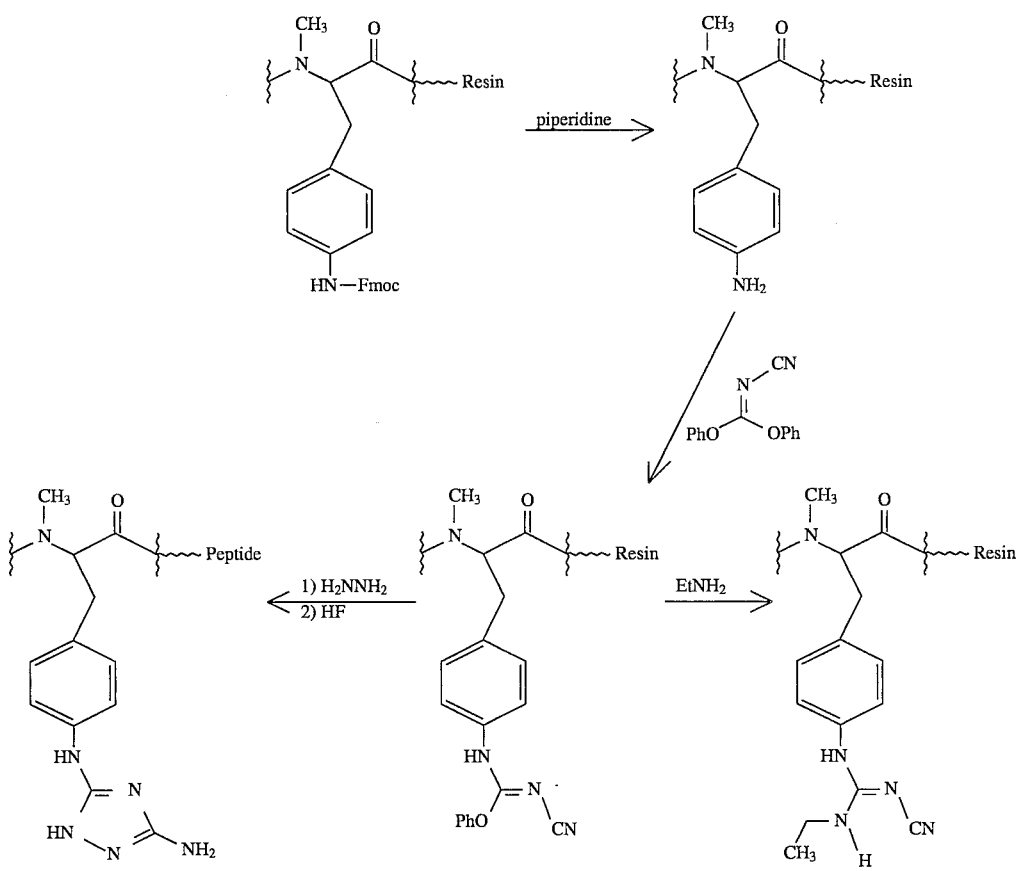

Scheme 2

EXAMPLE 4

NAc—D-2Nal—D-4ClPhe—D-3Pal—Ser—NMeTyr—
D-(4-Atza)Phe—Leu—Lys(Isp)—Pro—
D—AlaNH$_2$ The procedure described in Example 3 is used but substituting BOC—N—Me— Tyr(O-3-Br—Cbz) for BOC—NMe—(4-N-FMOC)Phe, and BOC—D—(4-N-FMOC)Phe for BOC—DLys(Nic). Upon the completion of the synthesis the peptide-resin is treated with 30% piperidine/DMF for 2 to 24 hr, to cleave the FMOC protecting group from the 4-amino group on the NMe—D—Phe$^6$ residue. The peptide-resin is washed, 3 times with methylene chloride, 3 times with DMF, and reacted with 10to 20-fold excess of diphenylcyanoarboimidate in DMF overnight, washed, 3 times with methylene chloride, 3 times with DMF, and then reacted with 20- to 100-fold excess of hydrazine in DMF

EXAMPLE 5

NAc—D-2Nal—D-4ClPhe—D-3Pal—Ser—NMe—
(4-Atza)Phe—D—(4-Atza)Phe—Leu
—Lys(Isp)—Pro—D—AlaNH$_2$ The procedure described in Example 4 is used but substituting BOC—NMe(4-FMOC-amino)Phe for BOC—NMeTyr(O-3Br-Cbz) Upon the completion of the synthesis the peptide-resin is treated with 30% piperidine/DMF for 2 to 24 hr, to cleave the FMOC protecting groups from the 4-amino groups of the NMe—Phe$^5$ and the D—Phe$^6$ residues. The peptide-resin is washed 3 times with methylene chloride, 3 times with DMF, and reacted with 10- to 20-fold excess of diphenylcyanoarboimidate in DMF overnight, washed 3 times with methylene chloride, 3 times with DMF, and then reacted with 20- to 100-fold excess of hydrazine in DMF overnight. The peptide-resin is washed again, as previously described, dried over P₂O₅ overnight, and treated with HF/anisole as above. After work-up and lyophilization the crude product is obtained. This product is purified by HPLC to yield NAc—D2Nal—D4ClPhe—D3Pal—Ser—NMe—(4-Atza)Phe—D—(4-Atza)Phe— Leu—Lys(Isp)—Pro—D AlaNH₂. R$_t$=14.83 min; FAB Mass Spec. m/e 1626 (M+H). Amino acid anal.: 1.01 Ala; 1.00 Pro; 0.89 LysClsp); 1.00 Leu; 1.00 Lys; 0.5 Ser; 1.02 3Pal; 0.92 4ClPhe.

EXAMPLE 6

NAc—D-2Nal—D—ClPhe—D-3 Pal—Ser—NMe—(4. Atza)Phe—D—Lys(Nic)—Leu—Asg— Pro—D AlaNH₂

The procedure described in Example 3 is used but substituting BOC—Arg(Tos) for BOC—Lys(Isp,Cbz). Upon the completion of the synthesis the peptide resin is dried over P₂O₅ overnight and then treated with HF/anisole, as described above, to cleave the peptide from the resin and the protecting groups. After work-up, lyophilization and HPLC purification NAc—D2Nal—D4ClPheD— D3Pal—Ser—NMe(4-Atza)Phe—DLys(Nic)—Leu—Arg—Pro—DAlaNH₂ is obtained.

EXAMPLE 7

NAc—D-2Nal—D-4ClPhe—D-3Pal—Ser—NMeTyr—D—(4-Atza)Phe—Leu—Arg—Pro—DAlaNH₂

The procedure described in Example 4 is used but substituting BOC—ArgCTos) for BOC—Lys(Isp,Cbz). Upon the completion of the synthesis the peptide resin is dried over P₂O₅ overnight and then treated with HF/anisole, as described above, to cleave the peptide from the resin and the protecting groups. After work-up, lyophilization and HPLC purification NAc—D-2Nal—D-4ClPhe—D 3Pal—Ser—NMeTyr—D—(4-Atza)Phe—Leu—Arg—Pro—DAlaNH₂ is obtained.

EXAMPLE 8

NAc—D2 Nal—D4ClPhe—D3 Pal—Ser—NMe—(4-Atza)Phe—D—(4-Atza)Phe—Leu—Arg—Pro—D—AlaNH₂

The procedure described in Example 5 is used but substituting BOC—Arg(Tos) for BOC—Lys(Isp,Cbz). Upon the completion of the synthesis the peptide resin is dried over P₂O₅ overnight and then treated with HF/anisole, as described above, to cleave the peptide from the resin and the protecting groups. After work-up, lyophilization and HPLC purification NAc—D-2Nal—D4ClPhe—D 3Pal—Ser—NMe—(4-Atza)Phe—D(4-Atza)Phe—Leu—Arg—Pro—DAlaNH₂ is obtained.

EXAMPLE 9

NAc—Sar—D4ClPhe—D1Nal—Ser—NMe—(4-Atza)Phe—D—(4-Atza)Phe—Leu—Lys(Isp)—Pro—DAlaNH₂

The procedure described in Example 3 is used but substituting BOC—Sar for BOC—D-2-Nal and BOC—D-1-Nal for BOC—D-3-Pal. Upon the completion of the synthesis the peptide resin is dried over P₂O₅ overnight and then treated with HF/anisole, as described above, to cleave the peptide from the resin and the protecting groups. After work-up, lyophilization and HPLC purification NAc—SarD 4ClPhe—D1Nal—Ser—NMe—(4-Atza)Phe—D—(4-Atza)Phe—Leu—Lys(Isp)—Pro— DAlaNH₂ is obtained.

EXAMPLE 10

NAc—D2Nal—D4ClPhe—D3Pal—Ser—NMe(4-Morphme)Phe—DLys(Nic)—Leu—Lys(Isp)—Pro—DAlaNH₂

The procedure described in Example 3 is used but substituting BOC—N—Me—(4-N-FMOC)Phe with BOC—N—Me(4-morpholinomethyl)Phe tosylate salt and extending the coupling time in the synthesis protocol to two-6hr. After treatment with HF/anisole, lyophilization and HPLC purification, as described above NAc—D 2Nal—D4ClPhe—D3Pal—Ser—NMe(4-Morphme)Phe—DLys-(Nic)—Leu—Lys(Isp)—Pro— DAlaNH₂ is obtained.

EXAMPLE 11

NAc—D2Nal—D4ClPhe—D3Pal—Ser—NMe(4-Morphme)Phe—D—(4-Morphme)Phe—LeU—Lys(Isp)—Pro—DAlaNH₂

The procedure described in Example 10 is used but substituting BOC—D—(4-morpholinomethyl)Phe for BOC—D—Lys(Nic). After treatment of the peptide-resin with HF/anisole, work-up of the reaction, lyophilization and purification of the product NAc—D2Nal—D4ClPhe—D3Pal—Ser—NMe(4-Morphme)Phe—D—(4-Morphme)Phe—Leu—Lys(Isp)—Pro—DAlaNH₂ is obtained.

EXAMPLE 12

NAc—D2Nal—D4ClPhe—D3Pal—Ser—NMe—Tyr—D—(4-Morphme)Phe—Leu—Lys(Isp)—Pro—DAlaNH₂

The procedure described in Example 11 is used but substituting BOC—N—Me— Tyr(O-3-Br-Cbz) for BOC—N—Me(4-morpholino-N'-methyl)Phe tosylate. After treatment of the peptide-resin with HF/anisole, work-up of the reaction, lyophilization and purification of the product NAc—D2Nal—D4ClPhe—D3Pal—Ser— NMeTyr—D—(4-Morphme)Phe—Leu—Lys(Isp)—Pro—DAlaNH₂ is obtained.

EXAMPLE 13

NAc—D2 Nal—D4ClPhe—D3 Pal—Ser—NMe (4-Morphme)Phe—D Lys(Nic)—Leu—Arg—Pro—DAlaNH₂

The procedure described in Example 10 is used but substituting BOC—Arg(Tos) for BOC—Lys(Isp,Cbz). After treatment of the peptide-resin with HF/anisole, work-up of the reaction, lyophilization and purification of the product NAc—D2Nal—D4ClPhe—D3 Pal—Ser—NMe(4-Morphme)Phe—DLys(Nic)—Leu—Arg—Pro— DAlaNH₂ is obtained.

EXAMPLE 14

The procedure described in Example 10 is used but substituting the appropriate BOC-amino acids described in Preparation D instead of BOC—N—Me— 4-(morpholino-N'-methyl)Pherosylate. After work-up and HPLC purification the following compounds are obtained:

NAc—D2Nal—D4ClPhe—D3Pal—Ser—NMe-4(piperidino-N'-methyl)Phe—DLys(Nic)— Leu—Arg—Pro—DAlaNH$_2$.

NAc—D2Nal—D4ClPhe—D3Pal—Ser—NMe-4(pyrrolidino-N'-methyl)Phe—DLys(Nic)— Leu—Arg—Pro—DAlaNH$_2$.

NAc—D2Nal—D4ClPhe—D3Pal—Ser—NMe-4-(N'-acetyl-N''-piperazino-methyl)Phe— DLys(Nic)—Leu—Arg—Pro—DAlaNH$_2$.

NAc—D2Nal—D4ClPhe—D3Pal—Ser—NMe-4-(diethyl-N'-methyl)Phe—DLys(Nic)—Leu— Arg—Pro—DAlaNH$_2$.

NAc—D2Nal—D4ClPhe—D3Pal—Ser—NMe-4-(di-t-butyl-N'-methyl)Phe—DLys(Nic)— Leu—Arg—Pro—DAlaNH$_2$.

NAc—D2Nal—D4ClPhe—D3Pal—Ser—NMe-4-(di-methyl-N'-methyl)Phe—DLys(Nic)— Leu—Arg—Pro—DAlaNH$_2$.

NAc—D2 Nal—D4ClPhe—D3Pal—Ser—NMe-4-(di-isopropyl-N'-methyl)Phe— DLys(Nic)—Leu—Arg—Pro—D AlaNH$_2$.

NAc—D2Nal—D4ClPhe—D3Pal—Ser—NMe-4-(di-propyl-N'-methyl)Phe—DLys(Nic)— Leu—Arg—Pro—DAlaNH$_2$.

NAc—D2Nal—D4ClPhe—D3Pal—Ser—NMe-4-(propyl-N'-methyl)Phe—DLys(Nic)—Leu— Arg—Pro—DAlaNH$_2$.

NAc—D2Nal—D4ClPhe—D3Pal—Ser—NMe-4-(ethyl-N'-methyl)Phe—DLys(Nic)—Leu— Arg—Pro—DAlaNH$_2$.

NAc—D2Nal—D4ClPhe—D3Pal—Ser—NMe-4-(phenyl-N'-methyl)Phe—DLys(Nic)—Leu— Arg—Pro—DAlaNH$_2$.

NAc—D2Nal—D4ClPhe—D3Pal—Ser—NMe-4-(benzyl-N'-methyl)Phe—DLys(Nic)—Leu— Arg—Pro—DAlaNH$_2$.

NAc—D2Nal—D4ClPhe—D3Pal—Ser—NMe-4-(p-chlorobenzyl-N'-methyl)Phe— DLys(Nic)—Leu—Arg—Pro—DAlaNH$_2$.

NAc—D2Nal—D4ClPhe—D3Pal—Ser—NMe-4-(p-fluorobenzyl-N'-methyl)Phe— DLys(Nic)—Leu—Arg—Pro—D AlaNH$_2$.

NAc—D2 Nal—D4ClPhe—D3Pal—Ser—NMe-4-(p-nitrobenzyl-N'-methyl)Phe— DLys(Nic)—Leu—Arg—Pro—DAlaNH$_2$.

EXAMPLE 15

NAc—Sar—D4ClPhe—D1Nal—Ser—NMe—(4-Atza)Phe—D—Lys(Nic)-Leu—Lys(Isp)—Pro—DAlaNH$_2$ The procedure described in Example 9 is used but substituting BOC—Lys(Nic) for BOC—D—(4-Atza)Phe. After treatment of the peptide-resin with HF/anisole, work-up of the reaction, lyophilization and purification of the product NAc—Sar—D 4ClPhe—D1Nal—Ser—NMe—(4-Atza)Phe—D—Lys(Nic)—Leu—Lys(Isp)—Pro—DAlaNH$_2$.

EXAMPLE 16

NAc-D2Nal—D4ClPhe—D3Pal—Ser—NMe(4-Atzame)Phe—D Lys(Nic)-Leu—Lys(Isp)—Pro—DAlaNH$_2$ The procedure described in Example 3 is used but substituting BOC—NMe-[4-(FMOC)-aminomethyl] -Phe instead of BOC—NMe-[4-FMOC-amino]-Phe. After work-up, lyophilization and HPLC purification NAc—D2Nal—D4ClPhe—D3Pal—Ser—NMe( 4-Atzame)Phe—DLys-(Nic)—Leu—Lys(Isp)—Pro—DAlaNH$_2$ is obtained.

EXAMPLE 17

NAc—D2Nal—D4ClPhe—D3Pal—Ser—NMe(4-Atzame)Phe—DLys(Nic)—Leu—Lys(Isp)—Pro—DAlaNH$_2$ The procedure described in Example 16 is used but substituting BOC—D—[4-(FMOC)-aminomethyl] -Phe instead of BOC-DLys(Nic). After work-up, lyophilization and HPLC purification NAc—D2Nal—D4ClPhe—D3Pal—Ser—NMe(4-Atzame)Phe— D—(4-Atzame)Phe—Leu—Lys(Isp)—Pro—DAlaNH$_2$ is obtained.

EXAMPLE 18

NAc—D2Nal—D4ClPhe—D-3Pal—Ser—NMe(4-Atza)Phe—DLys(Nic)—Leu—Harg(Et$_2$)—Pro—DAlaNH$_2$ The procedure described in Example 3 is used but substituting BOCHarg(Et$_2$) tosylate salt instead of BOC—Lys(Isp,Cbz). After work-up, lyophilization and HPLC purification NAc—D2Nal—D4ClPhe—D3Pal—Ser—NMe(4-Atza)Phe— DLys(Nic)—Leu—Harg(Et$_2$)—Pro—DAlaNH$_2$ is obtained.

EXAMPLE 19

NAc—D2Nal—D4ClPhe—D3Pal—Ser—NMe(4-Atza)Phe—D—(4-Atza)Phe—Leu—Harg(Et$_2$)—Pro—D AlaNH$_2$ The procedure described in Example 18 is used but substituting BOC—D—(4-Atza)Phe instead of BOC—D—Lys(Nic). After work-up, lyophilization and HPLC purification NAc—D2Nal—D4ClPhe—D3Pal—Ser—NMe(4-Atza)Phe—D—(4-Atza)Phe— Leu—Harg(Et$_2$)—Pro—DAlaNH$_2$ is obtained.

EXAMPLE 20

The procedure described in Example 9 is used but substituting the appropriate protected amino acids, which were described above. After work-up, lyophilization and HPLC purification NAc—Sar—D4ClPhe—D1Nal—Ser—NMe(4-Atza)Phe— D—Lys(Nic)—Leu—Lys(Isp)—Pro—DAlaNH$_2$ and After work-up, lyophilization and HPLC purification NAc—Sar—D4ClPhe—D1Nal—Ser—NMeTyr—D—( 4-Atza)Phe—Leu—Lys(Isp)—Pro—DAlaNH$_2$ are obtained.

EXAMPLE 21

The procedures described in Examples 9 and 20 are used but substituting BOC—D-3-Bal instead of BOC—D-1-Nal. After work-up, lyophilization and HPLC purification the following compounds are obtained:

NAc—Sar—D4ClPhe—D3Bal—Ser—NMe—(4-Atza)Phe—D—(4-Atza)Phe—Leu—Lys(Isp)— Pro—DAlaNH$_2$.

NAc—Sar—D4ClPhe—D3Bal—Ser—NMe(4-Atza)Phe—D—Lys(Nic)—Leu—Lys(Isp)—Pro— DAlaNH$_2$.

NAc—Sar—D4ClPhe—D3Bal—Ser—NMe Tyr—D—(4-Atza)Phe—Leu—Lys(Isp)—Pro— DAlaNH$_2$.

EXAMPLE 22

The procedures described in Examples 21 are used but substituting BOC— D-1-Nal instead of BOC—D-3-Bal, BOC—NMe—(4-Atzame)Phe instead of BOC— NMe—(4-Atza)Phe, and BOC—D—(4-Atzame)Phe instead of BOC—D—(4-Atza)Phe. After work-up, lyophilization and HPLC purification the following compounds are obtained:

NAc—Sar—D4ClPhe—D-1Nal—Ser—NMe—(4-Atzame)Phe—D—(4-Atzame)Phe—Leu— Lys(Isp)—Pro—DAlaNH$_2$.

NAc—Sar—D4ClPhe—D-1Nal—Ser—NMe(4-Atzame)Phe—D—Lys (Nic)—Leu—Lys(Isp)— Pro—D AlaNH$_2$.

NAc—Sar—D4ClPhe—D-1Nal—Ser—NMeTyr—D—(4-Atzame)Phe—Leu—Lys(Isp)—ProDAlaNH$_2$.

EXAMPLE 23

The procedures described in Examples 22 is used but substituting BOC—D— 3-Bal instead of BOC—D-1-Nal. After work-up, lyophilization and HPLC purification the following compounds are obtained:

NAc—Sar—D4ClPhe—D-3Bal—Ser—NMe—(4-Atzame)Phe—D—(4-Atzame)Phe—Leu— Lys(Isp)—Pro—DAlaNH$_2$.

NAc—Sar—D4ClPhe—D-3Bal—Ser—NMe(4-Atzame)Phe—D—Lys(Nic)—Leu—Lys(Isp)— Pro—DAlaNH$_2$.

NAc—Sar—D4ClPhe—D-3Bal—Ser—NMe Tyr—D—(4-Atzame)Phe—Leu—Lys(Isp)—ProDAlaNH$_2$.

EXAMPLE 24

NAc—D-2-Nal—D-4—Cl—Phe—D-3-Pal—Ser—NMeTyr—D—(4-Imame)—Phe—Leu—Lys(Isp)—Pro—DAlaNH$_2$ The procedure described in Example 5 is used but substituting BOC—D—(4-FMOC-aminomethyl)Phe for BOC—D—(4-FMOC-amino)Phe. Upon completion of the synthesis the resin is treated overnight with 30% piperidine to remove the FMOC group, washed several times with CH$_2$Cl$_2$, then treated with excess 1,1'-thiocarbonyldiimidazole in DMF for 1 hr (see Scheme 3 below). The resin is washed again and treated with excess of N-BOC-ethylenediamine in (1:1) CH$_2$Cl$_2$/DMF for 4–24 hr. The solution is drained, the resin is washed several times with CH$_2$Cl$_2$ and then is treated with excess of CH$_3$I in (1:1) CH$_2$Cl$_2$/DMF for 4–24 hr. The BOC protecting group is removed by standard deblocking and base wash conditions and the resin is treated with 10% diisopropylethylamine/CH$_2$Cl$_2$ for 24 h. The solution was drained, the resin is washed, dried over P$_2$O$_5$ and treated with HF/anisole. After work-up, lyophilization and HPLC purification NAc—D-2-Nal—D-4-ClPhe—D-3-Pal—Ser— NMeTyr—D—(4-Imame)Phe—Leu—Lys(Isp)—Pro—D—AlaNH$_2$ is obtained.

Scheme 3

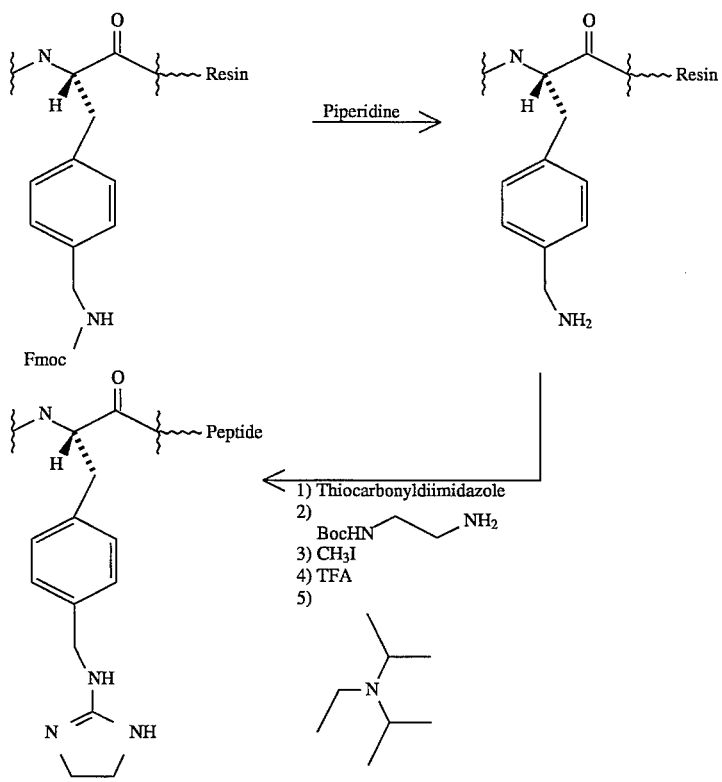

EXAMPLE 25

NAc—D-2-Nal—D-4-Cl—Phe—D-3-Pal—Ser—NMe—(4-Imame)Phe—D—Lys(Nic)—Leu—Lys(Isp)—Pro—D AlaNH$_2$ The procedure described in Example 24 is used but substituting BOC—NMe—(4-FMOC-aminomethyl)Phe for BOC—NMeTyr(O-3Br-Cbz) and BOC—DLys(Nic) for BOC—D—(4-FMOC-amino)Phe. Upon completion of the synthesis the peptide is cleaved with HF/anisole, worked-up, lyophilized, and purified by HPLC to yield NAc—D-2-Nal—D-4—Cl—Phe—D-3-Pal—Ser—NMe—(4-Imame)Phe—D—Lys(Nic)—Leu— Lys(Isp)—Pro—DAlaNH₂.

EXAMPLE 26

NAc—D-2-Nal—D-4—Cl—Phe—D-3-Pal—Ser—NMe—(4-Imame)Phe—
D—(4-Imame)Phe—Leu—Lys(Isp)—Pre—DAlaNH₂

The procedure described in Example 25 is used but substituting BOC—D—(4-FMOC-amino)Phe for BOC-DLys(Nic). Upon completion of the synthesis the peptide is cleaved with HF/anisole, worked-up, lyophilized, and purified by HPLC to yield NAc—D-2-Nal—D-4—Cl—Phe—D-3-Pal—Ser—NMe—(4-Imame)Phe—D—(4-Imame)Phe—Leu—Lys(Isp)—Pro—DAlaNH₂.

EXAMPLE 27

NAc—D-2-Nal—D-4—Cl—Phe—D-3-Pal—Ser—NMe-Tyr—D—(4-Nicme)Phe—Leu—Lys(Isp)—Pro—DAlaNH₂

The procedure described in Example 4 is used but substituting BOC—D—(4-FMOC-aminomethyl)Phe for BOC—D—(4-FMOC-amino)Phe. Upon the completion of the synthesis the FMOC group is removed upon treatment with 30% piperidine/DMF and the free amino group of the D-(4-aminomethyl)Phe⁶ residue of the peptide resin is coupled with nicotinic acid using the two-6 hr protocol. The resin is dried and treated with HF/anisole. After work-up, lyophilization, and HPLC purification NAc—D-2-Nal—D-4—Cl—Phe—D-3-Pal—Ser—NMe-Tyr—D—(4-Nicme)Phe—Leu—Lys(Isp)—Pro—D AlaNH₂.

EXAMPLE 28

NAc—D-2-Nal—D-4—Cl—Phe—D-3-Pal—Ser—NMe—Tyr—D—(4-Niceth)Phe—Leu—Lys(Isp)Pro—DAlaNH₂

The procedure described in Example 27 is used but substituting BOC—D—(4-FMOC-aminoethyl)Phe for BOC—D—(4-FMOC-aminomethyl)Phe. Upon the completion of the synthesis the FMOC group is removed upon treatment with 30% piperidine/DMF and the free amino group of the D-(4-aminoethyl)Phe⁶ residue of the peptide resin is coupled with nicotinic acid using the two-6 hr protocol. The resin is dried and treated with HF/anisole. After work-up, lyophilization, and HPLC purification NAc—D-2-Nal—D-4—Cl—Phe—D-3-Pal—Ser—NMe-Tyr—D—(4-Niceth) Phe—Leu—Lys(Isp)—Pro—DAlaNH₂.

EXAMPLE 29

NAc—D-2-Nal—D-4—Cl—Phe—D-3-Pal—Ser—NMe—(4-Nicme)Phe—D—(4-Nicme)Phe—Leu—Lys(Isp)—Pro—D AlaNH2

The procedure described in Example 27 is used but substituting BOC— NMe—(4-FMOC-aminomethyl)Phe for BOC—NMe-Tyr(O-3-Br—Cbz). Upon the completion of the synthesis the FMOC group is removed upon treatment with 30% piperidine/DMF and the free amino group of the D-(4-aminomethyl)Phe⁶ residue of the peptide resin is coupled with nicotinic acid using the two-6 hr protocol. The resin is dried and treated with HF/anisole. After work-up, lyophilization, and HPLC purification NAc—DNa—Nal—D-4—Cl—Phe—D-3-Pal—Ser—NMe—(4-Nicme)Phe—D-(4-Nicme)Phe—Leu—Lys(Isp)—Pro—DAlaNH2.

EXAMPLE 30

NAc—D-2-Nal—D-4—Cl—Phe—D-3-Pal—Ser—NMe—(4-Niceth)Phe—
D—(4-Niceth)Phe—Leu—Lys(Isp)—Pro—D AlaNH2

The procedure described in Example 29 is used but substituting BOC— NMe—(4-FMOC-aminoethyl)Phe for BOC—NMe—(4-FMOC-aminomethyl)Phe and BOC—D—(4-FMOC-aminoethyl)Phe for BOC—D—(4-FMOC-aminomethyl)Phe. Upon the completion of the synthesis the FMOC group is removed upon treatment with 30% piperidine/DMF and the free amino group of the D-(4-aminomethyl)Phe 6 residue of the peptide resin is coupled with nicotinic acid using the two-6 hr protocol. The resin is dried and treated with HF/anisole. After workup, lyophilization, and HPLC purification NAc—D-2-Nal—D-4—Cl—Phe—D-3-Pal—Ser— NMe—(4-Niceth)Phe—D—(4-Niceth)Phe—Leu—Lys(Isp)—Pro—DAlaNH2.

EXAMPLE 31

NAc—D2Nal—D4ClPhe—D3Pal—Ser—NMe(4-Etcng)Phe—DLys(Nic)—Leu—Lys(Isp)—Pro—DAlaNH2

The procedure described in Example 3 is used but substituting ethylamine for hydrazine and extending the reaction time from 24 to 72 hr. The resin is dried and treated with HF/anisole. After work-up, lyophilization, and HPLC purification NAc—D2Nal—D4ClPhe—D3Pal—Ser—NMe(4-Etcng)Phe—DLys(Nic)—Leu— Lys(Isp)—Pro—D AlaNH2.

EXAMPLE 32

NAc—D-2Nal—D-4ClPhe—D-3Pal—Ser—NMeTyr—D-(4-Etcng)Phe—Leu—Lys(Isp)—Pro—D-AlaNH₂

The procedure described in Example 4 is used but substituting ethylamine for hydrazine and extending the reaction time from 24 to 72 hr. The peptide-resin is dried over P₂O₅ overnight, and treated with HF/anisole as above. After work-up and lyophilization the crude product is obtained. This product is purified by HPLC to yield NAc—D-2Nal—D-4ClPhe—D-3Pal—Ser—NMeTyr—D—(4-Etcng)Phe—Leu— Lys(Isp)—Pro—D—AlaNH₂.

EXAMPLE 33

NAc—D-2 Nal—D-4ClPhe—D-3Pal—Ser—NMe—(4-Etcng)Phe—D-(4-Etcng)Phe—Leu—Lys(Isp)—Pro—D—AlaNH₂

The procedure described in Example 5 is used but substituting ethylamine for hydrazine and extending the reaction time from 24 to 72 hr. The peptide-resin is dried over P₂O₅ overnight, and treated with HF/anisole as above. After work-up and lyophilization the crude product is obtained. This product is purified by HPLC to yield NAc—D-2Nal—

D-4ClPhe—D-3Pal—Ser—NMe—(4-Etcng)Phe—D—(4-Etcng)Phe— Leu—Lys(Isp)—Pro—D—AlaNH$_2$.

We claim:

1. A compound or pharmaceutically acceptable salt thereof selected from the group consisting of
NAc—D-2Nal —D-4ClPhe—D-3Pal—Ser—NMe—(4-Atza)Phe—D—(4-Atza)Phe— Leu—Lys(Isp)—Pro—D—AlaNH$_2$;
NAc—D2Nal—D4ClPhe—D3Pal—Ser—NMe(4-Atza)Phe—DLys(Nic)—Leu— Lys(Isp)—Pro—D—AlaNH$_2$;
NAc—D-2Nal—D—4ClPhe—D-3-Pal—Ser—NMeTyr—D—(4-Atza)Phe—Leu— Lys(Isp)—Pro—D—AlaNH$_2$.

2. A pharmaceutical composition for supressing levels of sex hormones in a mammal comprising a a sex hormone suppressing effective amount of a compound as defined by claim 1 in combination with a pharmaceutically acceptable carrier.

3. A method of suppressing levels of sex hormones in a mammal in need of such treatment comprising administering a sex hormone suppressing effective amount of a compound as defined by claim 1.

* * * * *

UNITED STATES PATENT AND TRADEMARK OFFICE
CERTIFICATE OF CORRECTION

PATENT NO. : 5,491,217
DATED : February 13, 1996
INVENTOR(S) : F. Haviv, et. Al.

Page 1 of 2

It is certified that error appears in the above-indentified patent and that said Letters Patent is hereby corrected as shown below:

Column 1, line 29, change "His Trp" to --His-Trp--.

Column 3, line 36, change "(b) N-(R1)-L" to --(b) N-(R1)-L--.

Column 3, line 38, change "(g) ert-butylglycyl" to --(g) tert-butylglycyl--.

Column 3, line 43, change "(b) N-R1)-L-alanyl" to --(b) N-(R1)-L-alanyl--.

Column 3, line 45, change "(B) N-R1)-D-alani" to --(B) N-(R1)-D-alani--.

Column 3, line 46, change "(C) N-R1)-L-alaninamide" to --(C) N-(R1)-L-alaninamide--.

Column 4, line 11, change "iodo (D." to --iodo (I).--.

Column 14, line 32, change "carder" to --carrier--.

Column 15, line 38, change "Pres" to --Press--.

Column 16, line 21, change "o benzyl" to --benzyl--.

Column 17, line 8, change "carded" to --carried--.

Column 21, line 53, change "carded" to --carried--.

Column 21, line 58, change "DMF lo solution" to --DMF solution--.

Column 22, lines 41-42, change "D-3pa! .Ser" to -- D-3Pal-Ser --.

UNITED STATES PATENT AND TRADEMARK OFFICE
CERTIFICATE OF CORRECTION

PATENT NO. : 5,491,217
DATED : February 13, 1996
INVENTOR(S) : F. Haviv, et. Al.

It is certified that error appears in the above-indentified patent and that said Letters Patent is hereby corrected as shown below:

Column 22, line 61, change "(4-NO $_2$)Phe" to --(4-NO$_2$)Phe--.

Column 23, line 9, change "DLysCNic)" to --DLys(Nic)--.

Column 23, line 10, change "20.56 rain;" to --20.56 min;--.

Column 23, line 64, change "10to 20" to --10 to 20--.

Column 25, line 7, change "LysCsp);" to --Lys(Isp);--.

Column 25, line 13, change "Nme-(4." to --Nme-(4- --.

Column 25, line 14, change "Asg" to --Arg--.

Column 26, line 25, change "LeU" to --Leu--.

Column 26, line 67, change "N'-methyl)pherosylate" to --N'-methyl)Phe tosylate--.

Column 33, line 10, change "D-AlaNH$_2$" to --DAlaNH$_2$--.

Signed and Sealed this

Eighteenth Day of February, 1997

Attest:

BRUCE LEHMAN

*Attesting Officer*  *Commissioner of Patents and Trademarks*